(12) United States Patent
Tresch et al.

(10) Patent No.: US 11,453,708 B2
(45) Date of Patent: *Sep. 27, 2022

(54) DESIGNED ANKYRIN REPEAT PROTEINS BINDING TO HEPATOCYTE GROWTH FACTOR

(71) Applicant: Molecular Partners AG, Schlieren (CH)

(72) Inventors: Gaby Tresch, Wolfhausen (CH); Talitha Bakker, Birmensdorf (CH); Douglas Phillips, Baden (CH); Frieder W. Merz, Mellingen (CH); Kaspar H. Binz, Birmensdorf (CH)

(73) Assignee: MOLECULAR PARTNERS AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/891,792

(22) PCT Filed: Jun. 2, 2014

(86) PCT No.: PCT/EP2014/061368
§ 371 (c)(1),
(2) Date: Jan. 19, 2016

(87) PCT Pub. No.: WO2014/191574
PCT Pub. Date: Dec. 4, 2014

(65) Prior Publication Data
US 2016/0251404 A1    Sep. 1, 2016

(30) Foreign Application Priority Data
May 31, 2013   (EP) .................................. 13170056

(51) Int. Cl.
*C07K 14/47* (2006.01)
*C07K 14/475* (2006.01)
*A61K 38/00* (2006.01)

(52) U.S. Cl.
CPC .......... *C07K 14/47* (2013.01); *C07K 14/4753* (2013.01); *A61K 38/00* (2013.01); *C07K 2318/20* (2013.01)

(58) Field of Classification Search
CPC .............. C07K 14/475; C07K 14/4753; C07K 2318/20; A61K 38/00
See application file for complete search history.

(56) References Cited

U.S. PATENT DOCUMENTS

| | | |
|---|---|---|
| 7,417,130 B2 | 8/2008 | Stumpp et al. |
| 8,110,653 B2 | 2/2012 | Stumpp et al. |
| 8,710,187 B2 | 4/2014 | Binz et al. |
| 8,722,618 B2 | 5/2014 | Jacobs et al. |
| 8,846,577 B2 | 9/2014 | Steiner et al. |
| 8,901,076 B2 | 12/2014 | Binz et al. |
| 9,006,389 B2 | 4/2015 | Stumpp et al. |
| 2011/0224100 A1 | 9/2011 | Parmeggiani et al. |
| 2012/0177651 A1 | 7/2012 | Clarke et al. |
| 2013/0244940 A1 | 9/2013 | Steiner et al. |
| 2013/0296221 A1 | 11/2013 | Binz |
| 2014/0005125 A1 | 1/2014 | Baumann |
| 2014/0206599 A1 | 7/2014 | Baumann et al. |
| 2014/0221295 A1 | 8/2014 | Binz et al. |
| 2015/0057186 A1 | 2/2015 | Steiner et al. |
| 2015/0368302 A1* | 12/2015 | Baumann ............... C07K 14/47 514/8.1 |

FOREIGN PATENT DOCUMENTS

| | | | |
|---|---|---|---|
| CH | WO 2012149439 A2 * | 11/2012 | ............. C07K 14/47 |
| WO | 2006/105511 A1 | 10/2006 | |
| WO | 2012/149439 A2 | 11/2012 | |
| WO | WO 2014/083208 A1 | 6/2014 | |

OTHER PUBLICATIONS

Binz et al. High-affinity binders selected from designed ankyrin repeat protein libraries. Nature Biotechnology, 2004; 22: 575-582).*
Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. III:2129-2138, 1990.*
Lazar et al. Transforming Growth Factor alpha: Mutation of Aspartic Acid 47 and Leucine 48 Results in Different Biological Activities. Mol. Cell. Biol., 8:1247-1252, 1988.*
Bork. Powers and Pitfalls in Sequence Analysis: The 70% Hurdle. Genome Research, 2000; 10:398-400.*
Bork. Genome Research, 2000; 10:398-400 (Year: 2000).*
Binz et al. Nature Biotechnology, 2004; 22: 575-582 (Year: 2004).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Binz, H.K., et al., Designing repeat proteins: well-expressed, soluble and stable proteins from combinatorial libraries of consensus ankyrin repeat proteins. J Mol Biol. Sep. 12, 2003;332(2):489-503.
Binz, H.K., et al., High-affinity binders selected from designed ankyrin repeat protein libraries. Nat Biotechnol. May 2004;22(5):575-82. Epub Apr. 18, 2004.
Extended European Search Report for Application No. 13170056.9, dated Oct. 14, 2013 (10 pages).

(Continued)

*Primary Examiner* — Vanessa L. Ford
*Assistant Examiner* — Sandra Dillahunt
(74) *Attorney, Agent, or Firm* — Finnegan, Henderson, Farabow, Garrett & Dunner, LLP

(57) ABSTRACT

New designed ankyrin repeat proteins with binding specificity for HGF are described, as well as nucleic acids encoding such HGF binding proteins, pharmaceutical compositions comprising such proteins and the use of such proteins in the treatment of diseases.

22 Claims, 4 Drawing Sheets
Specification includes a Sequence Listing.

(56) References Cited

OTHER PUBLICATIONS

International Search Report for Application No. PCT/EP2014/061368, dated Aug. 4, 2014 (3 pages).
Toschi, L., et al., Single-agent and combination therapeutic strategies to inhibit hepatocyte growth factor/MET signaling in cancer. Clin Cancer Res. Oct. 1, 2008;14(19):5941-6. doi: 10.1158/1078-0432.CCR-08-0071.
Amstutz et al., "Intracellular Kinase Inhibitors Selected from Combinatorial Libraries of Designed Ankyrin Repeat Proteins", JBC (2005) 280(26), 24715-24722.
Amstutz et al., "Rapid selection of specific MAP kinase-binders from designed ankyrin repeat protein libraries," Protein Engineering, Design & Selection (2006) 19(5), p. 219-229.
Binz et al., "Crystal Structure of a Consensus-Designed Ankyrin Repeat Protein: Implications for Stability," PROTEINS: Structure, Function, and Bioinformatics (2006) 65:280-284.
Binz et al., "Designed Repeat Proteins—Molecules with Antibody-like Binding Properties," BIOforum Europe Apr. 2005,(2004) pp. 34-36, GIT VERLAG GmbH & Co. KG, Darmstadt.
Binz et al., "Engineering novel binding proteins from nonimmunoglobulin domains," Nature Biotechnology (2005) 23(10), p. 1257-1268.
Binz and Pluckthun, "Engineered proteins as specific binding reagents," Current Opinion in Biotechnology (2005) 16, p. 459-469.
Boersma and Pluckthun, "DARPins and other repeat protein scaffolds: advances in engineering and applications," Curr Opin Biotechnol (2011) 22(6), p. 849-857.
Eggel et al., "DARPins as Bispecific Receptor Antagonists Analyzed for Immunoglobulin E Receptor Blockage", J Mol Biol (2009) 393, p. 598-607.
Forrer et al., "A novel strategy to design binding molecules harnessing the modular nature of repeat proteins," FEBS Letters (2003) 539, p. 2-6.
Forrer et al., "Consensus Design of Repeat Proteins," ChemBioChem (2004) 5, p. 183-189.
Hanes and Pluckthun., "In vitro selection and evolution of functional proteins by using ribosome display," Proc Natl Acad Sci USA (1997) 94(10), p. 4937-4942.
He and Taussig, "Ribosome display: cell-free protein display technology," Brief Funct Genomic Proteomic (2002) 1(2), p. 204-12.
Interlandi et al., "Characterization and Further Stabilization of Designed Ankyrin Repeat Proteins by Combining Molecular Dynamics Simulations and Experiments," J Mol Biol (2008) 375, p. 837-854.
Ka We et al., "Isolation of Intracellular Proteinase Inhibitors Derived from Designed Ankyrin Repeat Proteins by Genetic Screening," J Biol Chem (2006) 281(52), p. 40252-40263.
Kohl et al., "Designed to be stable: Crystal structure of a consensus ankyrin repeat protein", PNAS (2003) 100(4), p. 1700-1705.
Kramer et al., "Structural Determinants for Improved Stability of Designed Ankyrin Repeat Proteins with a Redesigned C-Capping Module", J Mol Biol (2010) 404, p. 381-391.
Sennhauser and Grutter, "Chaperone-Assisted Crystallography with DARPins", Structure (2008) 16, p. 1443-1453.
Steiner et al., "Efficient Selection of DARPins with Sub-nanomolar Affinities using SRP Phage Display", J Mol Biol 2008, 382(5), p. 1211-1227 (incl. Supplement).
Stumpp and Amstutz, "DARPins: A true alternative to antibodies," Curr Opin Drug Discov Devel. (2007) 10(2), p. 153-159.
Stumpp et al., "Designing Repeat Proteins: Modular Leucine-rich Repeat Protein Libraries Based on the Mammalian Ribonuclease Inhibitor Family", J Mol Biol (2003) 332, 471-487.
Stumpp et al., "DARPins: A new generation of protein therapeutics", Drug Discovery Today (2008) 13(15-16), p. 695-701.
Theurillat et al., "Designed ankyrin repeat proteins: a novel tool for testing epidermal growth factor receptor 2 expression in breast cancer", Modern Pathology (2010), 23(9):1289-1297.
Veesler et al., "Crystal Structure and Function of a DARPin Neutralizing Inhibitor of Lactococcal Phage TP901-1. Comparison of DARPin and Camelid VHH Binding Mode.", J Biol Chem (2009) 284(44), p. 30718-30726.
Zahnd et al., "Efficient Tumor Targeting with High-Affinity Designed Ankyrin Repeat Proteins (DARPins): Effects of Affinity and Molecular Size", Cancer Res (2010) 70(4), p. 1595-1605 (incl. Supplement).
Zahnd et al., "A designed ankyrin repeat protein evolved to picomolar affinity to Her2," J Mol Biol (2007) 369(4), p. 1015-1028.
Zahnd et al., "Ribosome display: selecting and evolving proteins in vitro that specifically bind to a target," Nature Methods (2007) 4(3), p. 269-279.
Zahnd et al., "Selection and Characterization of Her2 Binding-designed Ankyrin Repeat Proteins," J Biol Chem (2006) 281(46), p. 35167-35175.
Sedgwick S.G., Smerdon S.J., "The ankyrin repeat: a diversity of interactions on a common structural framework," *Trends in Biochemical Sciences*, 1999; 24(8): 311-316.
Mosavi et al. "Consensus-derived structural determinants of the ankyrin repeat motif," *Proceedings of the National Academy of Science of the United States of America*, 2002; 99(25): 16029-16034.

\* cited by examiner

Fig. 7

```
                       1          1          2          3
              1........ .........  .........  .........  1..
SEQ ID NO: 12 HDYSGFTPLH LAAYYGHLEI VEVLLKHGAD VNA
SEQ ID NO: 13 FDDWGHTPLH LAARYGHLEI VEVLLKYGAD VNA
SEQ ID NO: 14 EDTEGYTPLH LAAMDGHLEI VEVLLKNGAD VNA
SEQ ID NO: 15 KYEDGLTPLH LAAFYGHLEI VEVLLRHGAD VNA
SEQ ID NO: 16 TDAWGHTPLH LAAYLGHLEI VEVLLKYGAD VNA
SEQ ID NO: 17 EDTEGYTPLH LAAMDGHLEI IEVLLKHGAD VNA
SEQ ID NO: 18 KDRYGDTPLH LAADIGHLEI VEVLLKAGAD VNA
SEQ ID NO: 19 EDYFGNTPLH LAASYGHLEI VEVLLKAGAD VNA
SEQ ID NO: 20 KDDYGNTPLH LAANTGHLEI VEVLLKAGAD VNA
SEQ ID NO: 21 HDTWGLTPLH LAAFHGHQEI VEVLLKHGAD VNA
SEQ ID NO: 22 QDFYGKTPLH LAALRGHLEI VEVLLKYGAD VNA
SEQ ID NO: 23 HDYLGLTPLH LAASDGHLEI VEVLLKHGAD VNA
SEQ ID NO: 24 YDYNGLTPLH LAANNGHLEI VEVLLKYGAD VNA
SEQ ID NO: 25 FDVAGYTPLH LAAYFGHLEI VEVLLKYGAD VNA
SEQ ID NO: 26 XDXXGXTPLH LAAXXGHLEI VEVLLKXGAD VNA
SEQ ID NO: 27 KDXXGXTPLH LAAXXGHLEI VEVLLKAGAD VNA
SEQ ID NO: 28 KDXXGXTPLH XAAXXGHLEI VEVLLKAGAD VNA
```

DESIGNED ANKYRIN REPEAT PROTEINS BINDING TO HEPATOCYTE GROWTH FACTOR

This application is the national stage entry under 35 U.S.C. § 371 of International Application No. PCT/EP2014/061368, filed on Jun. 2, 2014, which claims priority to European Application No. 13170056.9, filed on May 31, 2013. The contents of these applications are each incorporated herein by reference in their entirety.

FIELD OF THE INVENTION

The present invention relates to designed ankyrin repeat proteins with binding specificity for hepatocyte growth factor (HGF) as well as nucleic acids encoding such HGF binding proteins, pharmaceutical compositions comprising such proteins and the use of such proteins in the treatment of diseases.

BACKGROUND OF THE INVENTION

The MET proto-oncogene encodes a receptor tyrosine kinase (MET or c-Met) also known as hepatocyte growth factor receptor (HGFR; human HGFR has the UniProtKB/Swiss-Prot number P08581), which is essential for embryonic development and wound healing. Hepatocyte growth factor (HGF, also known as scatter factor; human HGF has the UniProtKB/Swiss-Prot number P14210) is the only known ligand of c-Met. The receptor is normally expressed by cells of epithelial origin, while expression of HGF is restricted to cells of mesenchymal origin. Upon HGF stimulation, c-Met induces several biological responses that collectively give rise to a program known as invasive growth. Abnormal c-Met activation in cancer correlates with poor prognosis, where aberrantly active c-Met triggers tumor growth, tumor cell survival, angiogenesis and metastasis. c-Met is deregulated in many types of human malignancies, including cancers of kidney, liver, stomach, breast, and brain and is a main driver for resistance to other targeted therapies (Bottaro, D. P., Rubin, J. S., Faletto, D. L., Chan, A. M., Kmiecik, T. E., Vande Woude, G. F. and Aaronson, S. A., Science 251(4995), 802-804, 1991; Comoglio, P. M, Giordano, S. and Trusolino, L., Nat. Rev. Drug Discov. 7(6), 504-516, 2008).

HGF is secreted as a single inactive single-chain precursor polypeptide (sc-HGF, sometimes also referred as pro-HGF) and is cleaved by serine proteases into a 69-kDa alpha-chain and 34-kDa beta-chain. Active HGF is a disulfide linked heterodimer consisting of the alpha- and beta-chain. HGF shares a high degree of homology with coagulation factors, as the alpha-chain contains plasminogen-like "kringle" structural motifs, and the beta-chain contains a domain homologous to serine proteases, but devoid of enzymatic activity (Naldini, L., Weidner, K. M., Vigna, E., Gaudino, G., Bardelli, A., Ponzetto, C., Narsimhan, R. P., Hartmann, G., Zarnegar, R., Michalopoulos, G. K., et al., EMBO J. 10, 2867-2878, 1991).

Through binding to its receptor, HGF mediates a number of cellular responses, including scattering of various cell types, the formation of tubules and lumens, epithelial-mesenchymal transition, angiogenesis, liver regeneration, wound healing and embryological development. The HGF/c-Met signaling pathway has also been shown to play a role in various diseases, among which many human solid tumors, in which it participates in tumor development, invasion and metastasis. In human cancers, both paracrine and autocrine activation of c-Met by HGF, the expression of these molecules in tumors and elevated concentrations of circulating HGF are associated with poor prognosis and increased risk of tumor metastasis (Comoglio et al., 2008, loc. cit.)

Because of the active role HGF in the development in cancer and other diseases, an agent blocking HGF activity could be beneficial in countering this effect. Various anti-HGF (aHGF) monoclonal antibodies (mAbs) are under clinical development at the moment, including AMG102 (i.e. rilotumumab), a humanized antihuman HGF IgG2 from Amgen, AV-299 from Schering/Aveo, and TAK-701 from Millennium.

There are, beside antibodies, novel binding proteins or binding domains that can be used to specifically bind a target molecule (e.g. Binz, H. K., Amstutz, P. and Plückthun, A., Nat. Biotechnol. 23, 1257-1268, 2005) and thereby act as an antagonist. One such novel class of binding proteins or binding domains not possessing an Fc are based on designed repeat proteins or designed repeat domains (WO 2002/020565; Binz, H. K., Amstutz, P., Kohl, A., Stumpp, M. T., Briand, C., Forrer, P., Grüner, M. G., and Plückthun, A., Nat. Biotechnol. 22, 575-582, 2004; Stumpp, M. T., Binz, H. K and Amstutz, P., Drug Discov. Today 13, 695-701, 2008). WO 2002/020565 describes how large libraries of repeat proteins can be constructed and their general application. Nevertheless, WO 2002/020565 does neither disclose the selection of repeat domains with binding specificity for HGF nor concrete repeat modules or repeat sequence motifs of repeat domains that specifically bind to HGF. Furthermore, WO 2002/020565 does not suggest that repeat domains with binding specificity for HGF could be used to regulate the HGF mediated signaling pathways to successfully treat diseases. These designed repeat domains harness the modular nature of repeat proteins and may possess N-terminal and C-terminal capping modules to prevent the designed repeat domains from aggregation by shielding the hydrophobic core of the domain (Forrer, P., Stumpp, M. T., Binz, H. K. and Plückthun, A., FEBS letters 539, 2-6, 2003).

The technical problem underlying the present invention is identifying novel binding proteins, such as ankyrin repeat proteins or domains, with binding specificity to HGF to regulate HGF mediated signaling pathways for an improved treatment of certain cancers, vascular disorders, angiogenesis related diseases and other pathological conditions. The solution to this technical problem is achieved by providing the embodiments characterized in the claims.

SUMMARY OF THE INVENTION

The present invention relates to a recombinant binding protein comprising at least one ankyrin repeat domain, wherein said ankyrin repeat domain binds HGF in PBS with a Kd below $10^{-7}$M.

More particularly, the invention relates to a recombinant binding protein comprising at least one ankyrin repeat domain, wherein said ankyrin repeat domain competes for binding to HGF with an ankyrin repeat domain selected from the group consisting of SEQ ID NOs:33 to 61

The invention further relates to a recombinant binding protein comprising at least one ankyrin repeat domain with binding specificity for HGF, which comprises an ankyrin repeat module having an amino acid sequence selected from the group consisting of SEQ ID NO:12 to 25 and sequences in which up to 9 amino acids in SEQ ID NO:12 to 25 are exchanged by any amino acid.

In particular, the invention relates to a recombinant binding protein comprising at least one ankyrin repeat domain that has at least 90% amino acid sequence identity with one ankyrin repeat domain selected from the group consisting of SEQ ID NOs:33 to 61 wherein G at position 1 and/or S at position 2 of said ankyrin repeat domain are optionally missing; and L at the second last position and/or N at the last position of said ankyrin repeat domain are optionally exchanged by A.

In particular the invention relates to a recombinant HGF binding protein comprising a peptide of any one of the sequences SEQ ID NO:12 to 25 and 33 to 62.

The invention further relates to nucleic acid molecules encoding the binding proteins of the present invention, and to a pharmaceutical composition comprising one or more of the above mentioned binding proteins or nucleic acid molecules.

The invention further relates to a method of treatment of a pathological condition using the binding proteins of the invention.

Surface Plasmon Resonance (SPR) analysis of DARPin binding to HGF (exemplified by DARPin #51). Various concentrations (1.6, 3.1, 6.3, 12.5 and 25 nM) of DARPin were applied to a flow cell with immobilized human HGF for 120 seconds, followed by washing with buffer flow. A global fit of the obtained traces resulted in a Kd value of 51 pM for the DARPin #51 interaction with human HGF. RU, Resonance Units; s, time in seconds. See below for the definition of DARPin #51.

Figure 2:
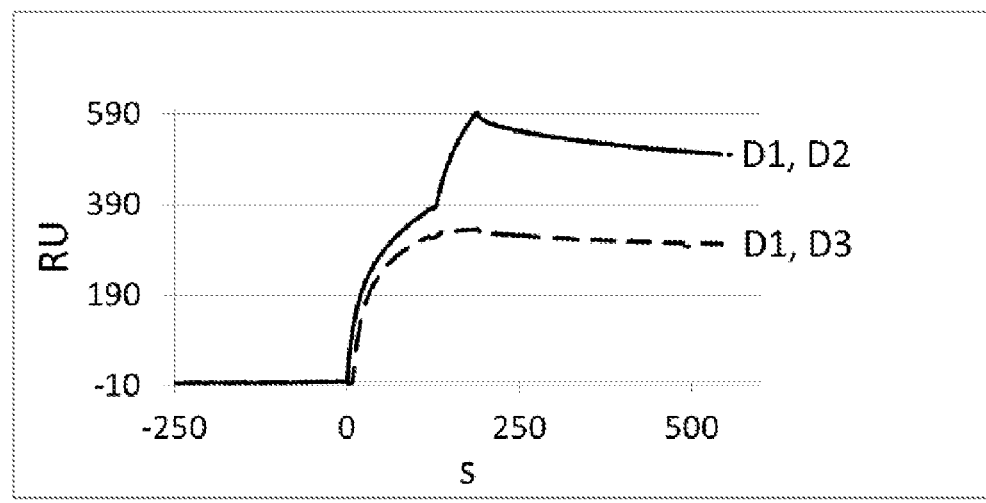

FIG. 2. Competition Surface Plasmon Resonance analysis.

SPR analysis of DARPins binding to human HGF (exemplified by DARPin #51, DARPin #57 and DARPin #43). 100 nM of DARPin #51 (i.e. D1) was applied to a flow cell with immobilized human HGF for 120 seconds, followed by injection of 100 nM of a second DARPin (either DARPin #57 or DARPin #33; i.e. D2 or D3, respectively) for 60 seconds. Thus, D1 and D3 compete for binding to HGF and D1 and D2 do not compete for binding to HGF.

RU, Resonance Units; s, time in seconds; D1, DARPin #51; D2, DARPin #57; D3, DARPin #33. See below for the definition of DARPin #51, DARPin #57 and DARPin #43.

Figure 3:
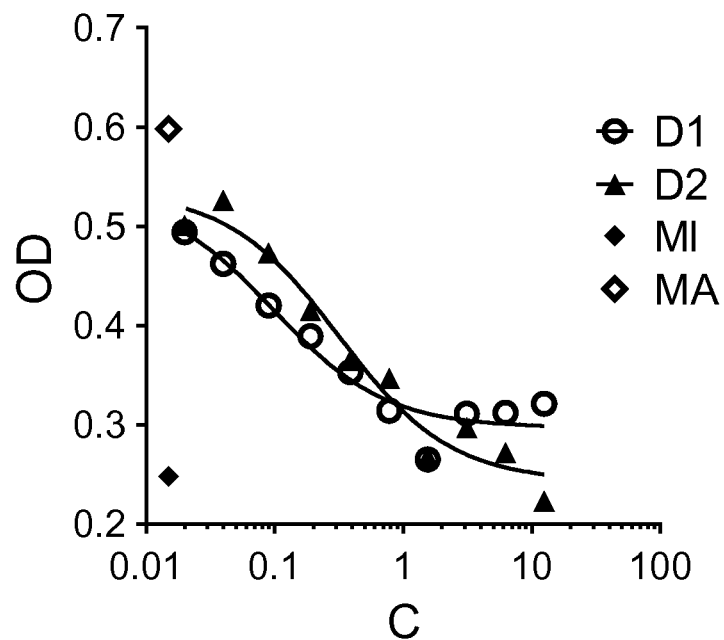

FIG. 3. Inhibition of HGF stimulated c-Met phosphorylation

The inhibition of the HGF stimulated c-Met phosphorylation in A549 cells by various concentrations of DARPins with specificity for human HGF (exemplified by DARPin #42 and #48) and corresponding fitted inhibition curves are shown. The $IC_{50}$ values were determined to be 0.32 and 0.1 nM for DARPin #42 and 48, respectively. OD, optical density at 450-620 nm; C, DARPin concentration in nM; D1, DARPin #48; D2, DARPin #42; MA, maximal activation; MI, minimal activation. The X axis is shown in logarithmic scale. See below for the definition of DARPin #52 and DARPin #48.

Figure 4:
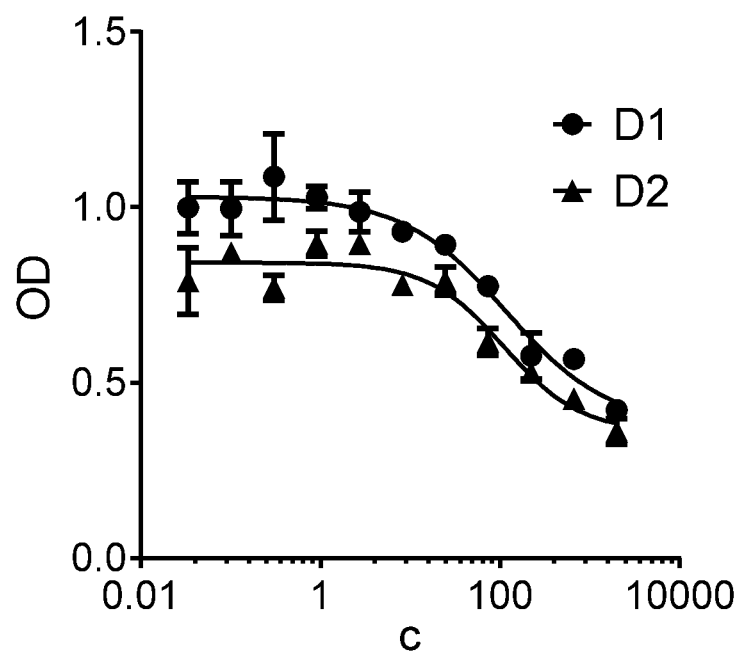

FIG. 4. Inhibition of U87 cell proliferation

The inhibition of the proliferation of U87 glioblastoma cells by various concentrations of DARPins with specificity for HGF (exemplified by DARPin #51 and #43) and corresponding fitted inhibition curves are shown. The $IC_{50}$ values were determined to be 72 and 116 nM for DARPin #43 and 51, respectively.

OD, optical density at 450-620 nm; C, DARPin concentration in nM; D1, DARPin #51; D2, DARPin #43. The X axis is shown in logarithmic scale. See below for the definition of DARPin #51 and DARPin #43.

Figure 5:
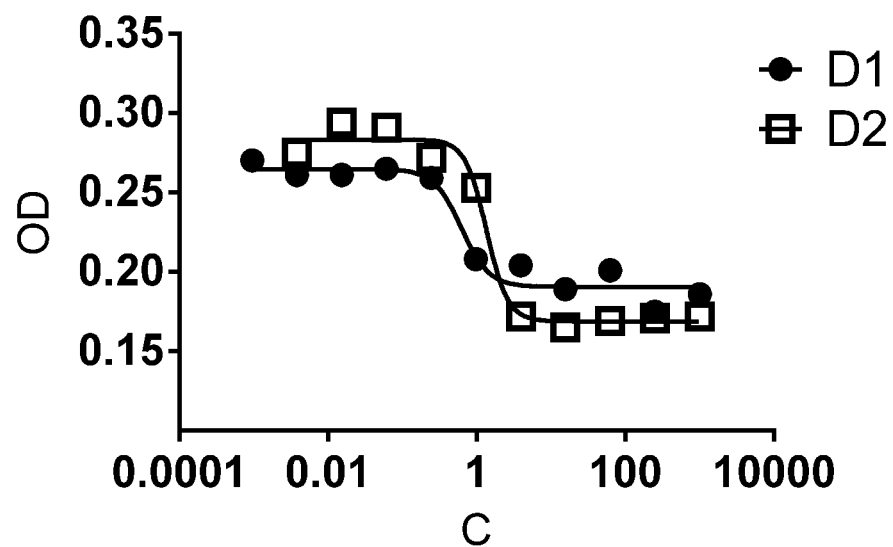

FIG. 5. c-Met competition assay.

The inhibition of the binding of HGF to c-Met by various concentrations of DARPins with specificity for human HGF and the corresponding fitted inhibition curves are shown for a distinct single experiment. The $IC_{50}$ values were then calculated to be about 1.36 and 0.62 nM for the DARPins #43 and #51, respectively. OD, optical density at 450-620 nm; C, concentration of DARPins in nM, D1, DARPin #51; D2, DARPin #43. The X axis is shown in logarithmic scale. See below for the definitions of DARPin #51 and 43.

Figure 6:
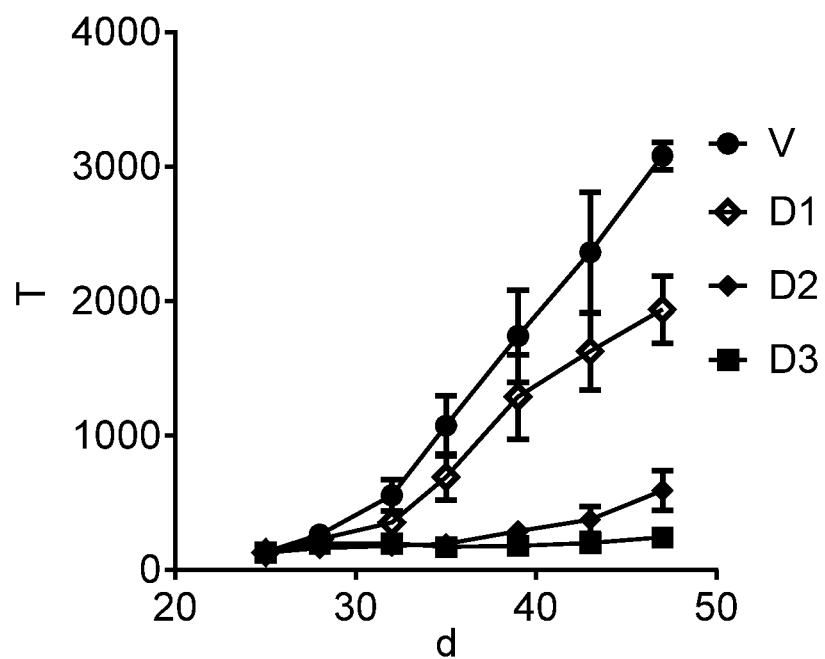

FIG. 6 Efficacy of an anti-HGF DARPin vs vehicle in a U87 tumor xenograft model.

U87-MG tumor cells were subcutaneously injected into nude mice. After tumor growth animals were randomized into four groups and treated with different concentrations (intravenous injection three-times a week, in total animals were dosed seven times) of PEGylated DARPins. The PEGylated DARPins were generated as described in Example 6.

T, tumor volume in $mm^3$; d, time in days; V, vehicle (i.e. PBS); D1, PEGylated DARPin #62 at a dose of 0.11 mg/kg per injection; D2, PEGylated DARPin #62 at a dose of 1.1 mg/kg per injection; D3, PEGylated DARPin #62 at a dose of 11 mg/kg per injection.

FIG. 7 Multiple sequence alignment of SEQ ID NOs: 12 to 28. SEQ ID NOs: 12 to 28 are aligned in a multiple alignment according to the residue position. The ankyin repeat residue position numbers are indicated at the top. Residue positions 2, 5, 7-13, and 16-33 correspond to positions which typically contain framework residues. Residue positions 1, 3, 4, 6, 14, and 15 correspond to positions which potentially contain target interaction residues.

DETAILED DESCRIPTION OF THE INVENTION

The recombinant binding protein or domain according to the invention is specific for a mammalian HGF. Preferably, the recombinant binding domain according to the invention is specific for a HGF of mice, rat, dog, rabbit, monkey or human origin. More preferably, the recombinant binding domain according to the invention is specific for a HGF of human origin.

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structures, is termed "protein domain". Such proteins or protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen), yeast expression plasmid or mammalian expression plasmid. When, for example, such a constructed recombinant bacterial expression plasmid is inserted into an appropriate bacteria (e.g. *Escherichia coli*), this bacteria can produce the polypeptide encoded by this recombinant DNA. The correspondingly produced polypeptide is called a recombinant polypeptide.

In the context of the present invention, the term "polypeptide" relates to a molecule consisting of one or more chains of multiple, i.e. two or more, amino acids linked via peptide bonds. Preferably, a polypeptide consists of more than eight amino acids linked via peptide bonds.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag of SEQ ID NO:9), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 2002/020565. Particular examples of such linkers are glycine-serine-linkers and proline-threonine-linkers of variable lengths; preferably, said linkers have a length between 2 and 24 amino acids; more preferably, said linkers have a length between 2 and 16 amino acids. An example of a glycine-serine-linker is provided in SEQ ID NO:10 and an example of a proline-threonine-linker is provided in SEQ ID NO:11. Preferably, the proline-threonine-linker of SEQ ID NO:11 is preceded by GS and/or followed by GS.

The term "polymer moiety" refers to either a proteinaceous polymer moiety or a non-proteinaceous polymer moiety. A "proteinaceous polymer moiety" preferably is a polypeptide that does not form a stable tertiary structure. Examples of proteinaceous polymer moieties are XTEN® (a registered trademark of Amunix; WO 2007/103515) polypeptides, or polypeptides comprising proline, alanine and serine residues as described in WO 2008/155134. Such proteinaceous polymer moieties can be covalently attached to, for example, a binding domain of the invention by the generation of genetic fusion polypeptides using standard DNA cloning technologies, followed by their standard expression and purification. A "non-proteinaceous polymer moiety" is a polymer moiety not built from polypeptides. Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention. A polymer moiety of the invention may vary widely in molecular weight. Preferably, said polymer moiety is connected by a polypeptide linker to a binding domain.

In a specific embodiment, a PEG moiety or any other non-proteinaceous polymer can, e.g., be coupled to a cysteine thiol via a maleimide linker with the cysteine being coupled via a peptide linker to the N or C terminus of a binding domain as described herein.

The term "binding protein" refers to a protein comprising one or more binding domains, one or more bioactive compounds and one or more polymer moieties as further explained below. Preferably, said binding protein comprises up to four binding domains. More preferably, said binding protein comprises up to two binding domains. Most preferably, said binding protein comprises only one binding domain. Furthermore, any such binding protein may comprise additional protein domains that are not binding domains, multimerization moieties, polypeptide tags, polypeptide linkers and/or one or more Cys residues. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. A Cys residue may be used for conjugating other moieties to the polypeptide, for example, by using the maleimide chemistry well known to the person skilled in the art. Preferably, said binding protein is a recombinant binding protein. Also preferably, the binding domains of binding protein possess different target specificities.

The term "bioactive compound" refers to a compound that is disease modifying when applied to a mammal having said disease. A bioactive compound may have antagonistic or agonistic properties and can be a proteinaceous bioactive compound or a non-proteinaceous bioactive compound. Such proteinaceous bioactive compounds can be covalently attached to, for example, a binding domain of the invention by the generation of genetic fusion polypeptides using standard DNA cloning technologies, followed by their standard expression and purification. Such non-proteinaceous bioactive compounds can be covalently attached to, for example, a binding domain of the invention by chemical means, e.g., by coupling to a cysteine thiol via a maleimide linker with a cysteine being coupled via a peptide linker to the N or C terminus of a binding domain as described herein. Examples of proteinaceous bioactive compounds are binding domains having a distinct target specificity (e.g. neutralizing a growth factor by binding to it), cytokines (e.g. interleukins), growth factors (e.g. human growth hormone), antibodies and fragments thereof, hormones (e.g. GLP-1), toxins (e.g. *Pseudomonas aeruginosa* exotoxin A) and any possible proteinaceous drug. Examples of non-proteinaceous bioactive compounds are, toxins (e.g. DM1 from ImmunoGen), small molecules targeting GPCRs, antibiotics and any possible non-proteinaceous drug.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Binz et al., 2005, loc. cit.). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display. Preferably, said binding domain is a recombinant binding domain.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In the particular application of the present invention, the target is HGF.

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

The definitions hereinafter for repeat proteins are based on those in patent application WO 2002/020565. Patent application WO 2002/020565 further contains a general description of repeat protein features, techniques and applications.

The term "repeat proteins" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create a superhelical structure having a joint hydrophobic core. Preferably, a repeat domain further comprises an N-terminal and/or a C-terminal capping unit (or module). Even more preferably, said N-terminal and/or C-terminal capping units (or modules) are capping repeats.

The term "designed repeat protein" and "designed repeat domain" refer to a repeat protein or repeat domain, respectively, obtained as the result of the inventive procedure explained in patent application WO 2002/020565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system. Accordingly, a designed ankyrin repeat protein (i.e. a DARPin) corresponds to a recombinant binding protein of the invention comprising at least one ankyrin repeat domain.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units correspond to the "repeating structural units (repeats)" of repeat proteins as described by Forrer et al., 2003, loc. cit. or the "consecutive homologous structural units (repeats)" of repeat proteins as described by Binz et al, 2004, loc. cit. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

Accordingly, the term "ankyrin repeat unit" shall mean a repeat unit, which is an ankyrin repeat as described, for example, by Forrer et al., 2003, loc. cit. Ankyrin repeats are well known to the person skilled in the art. The term "ankyrin repeat domain" refers to a repeat domain comprising two or more consecutive ankyrin repeat units (modules) as structural units, and, preferably, an N-terminal and/or a C-terminal capping unit (or module).

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (or module), or the influence on the polypeptide backbone conformation as found in α-helices or δ-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous to each other. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art. Further preferably, the repeat units used for the deduction of a repeat sequence motif are homologous repeat units obtained from repeat domains selected on a defined target.

The term "repeat sequence motif" refers to an amino acid sequence, which is deduced from one or more repeat units or repeat modules. Preferably, said repeat units or repeat modules are from repeat domains having binding specificity for the same target. Such repeat sequence motifs comprise framework residue positions and target interaction residue positions. Said framework residue positions correspond to the positions of framework residues of the repeat units (or modules). Typically, positions 2, 5, 7-13, and 16-33 of an ankyrin repeat contain framework residues. The numbering of positions of ankyrin repeats is shown in FIG. 7. Likewise, said target interaction residue positions correspond to the positions of target interaction residues of the repeat units (or modules). Typically, positions 1, 3, 4, 6, 14, and 15 of an ankyrin repeat potentially contain target interaction residues. Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues and/or the positions of target interaction residues that are specific for a certain target. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. Most often, such randomized positions correspond to the positions of target interaction residues. However, some positions of framework residues may also be randomized.

The term "folding topology" refers to the tertiary structure of said repeat units or repeat modules. The folding topology will be determined by stretches of amino acids forming at least parts of α-helices or β-sheets, or amino acid stretches forming linear polypeptides or loops, or any combination of α-helices, β-sheets and/or linear polypeptides/loops. For example, an ankyrin repeat unit/module consists of a β-turn, followed by two antiparallel α-helices and a loop that reaches the turn of the next repeat unit/module.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units (or modules). In most cases, repeat units (or modules) of a repeat domain will exhibit a high degree of sequence identity (same amino acid residues at corresponding positions) or sequence similarity (amino acid residues being different, but having similar physicochemical properties), and some of the amino acid residues might be key residues being strongly conserved. However, a high degree of sequence variability by amino acid insertions and/or deletions, and/or substitutions between the different repeat units (or modules) of a repeat domain may be possible as long as the common folding topology of the repeat units (or modules) is maintained.

Methods for directly determining the folding topology of repeat proteins by physicochemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins. Further preferably, each repeat module comprised in a repeat domain comprises a repeat sequence motif deduced from homologous repeat units obtained from repeat domains selected on the same target (e.g. HGF), for example as described in Example 1.

Accordingly, the term "ankyrin repeat module" shall mean a repeat module, which is originally derived from the repeat units of naturally occurring ankyrin repeat proteins. Ankyrin repeat proteins are well known to the person skilled in the art.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein said capping module forms tight tertiary interactions (i.e. tertiary structure interactions) with said repeat module thereby providing a cap that shields the hydrophobic core of said repeat module at the side not in contact with the consecutive repeat module from the solvent. Said N- and/or C-terminal capping module may be, or may be derived from, a capping unit or other structural unit found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary structure interactions with said repeat unit thereby providing a cap that shields the hydrophobic core of said repeat unit at one side from the solvent. Preferably, capping modules or capping units are capping repeats. The term "capping repeat" refers to a capping module or capping unit having a similar or the same fold as said adjacent repeat unit (or module) and/or sequence similarities to said adjacent repeat unit (or module). Capping modules and capping repeats are described in WO 2002/020565, WO 2012/069655 and by Interlandi et al., 2008 (loc. cit.). Examples of N-terminal ankyrin capping modules (i.e. N-terminal capping repeats) are SEQ ID NO:1 to 3 and examples of ankyrin C-terminal capping modules (i.e. C-terminal capping repeats) are SEQ ID NO:4 to 8.

For example, the N-terminal ankyrin capping module of SEQ ID NO:33 is encoded by the amino acids from position 1 to 32 and the C-terminal capping module of SEQ ID NO:33 is encoded by the amino acids form position 132 to 159.

A recombinant binding protein according to the invention comprises at least one ankyrin repeat domain, wherein said ankyrin repeat domain has binding specificity for mammalian HGF.

The term "has binding specificity for a target", "specifically binding to a target" or "target specificity" and the like means that a binding protein or binding domain binds in PBS to a target with a lower dissociation constant than to an unrelated protein such as the E. coli maltose binding protein (MBP). Preferably, the dissociation constant in PBS for the target is at least 10, more preferably at least $10^2$, even more preferably at least $10^3$, or most preferably at least $10^4$ times lower than the corresponding dissociation constant for MBP.

Recombinant binding proteins comprising an ankyrin repeat domain with binding specificity for HGF are shown in the Examples.

In particular, the invention relates to a recombinant binding protein as defined herein comprising at least one ankyrin repeat domain, wherein said ankyrin repeat domain specifically binds HGF (Hepatocyte Growth Factor).

Such specific binding refers to the selective affinity of the ankyrin repeat domains according to the invention for HGF. All ankyrin repeat domains that bind to HGF, or an epitope thereof, are deemed to specifically bind to that entity. Thus all ankyrin repeat domains that bind to HGF have binding specificity to the latter.

Preferably, said ankyrin repeat domain binds HGF in PBS with a dissociation constant (Kd) below $10^{-7}$M; more preferably, below $10^{-8}$M, $10^{-9}$M or $10^{-10}$M, or most preferably below $10^{-11}$M.

Methods to determine dissociation constants of protein-protein interactions, such as surface plasmon resonance (SPR) based technologies (e.g. SPR equilibrium or kinetic analysis) or isothermal titration calorimetry (ITC) are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

Example 2 shows how such $IC_{50}$ values of such ankyrin repeat inhibiting the inhibiting the binding of HGF to c-Met can be determined and recombinant binding proteins comprising an ankyrin repeat domain binding HGF with a Kd in PBS below $10^{-7}$M Preferred is a recombinant binding protein comprising an ankyrin repeat domain with binding specificity for human HGF.

Further preferred is a recombinant binding protein comprising an ankyrin repeat domain comprising between 70 and 300 amino acids, in particular between 90 and 200 amino acids.

A binding domain of the invention is an ankyrin repeat domain or a designed ankyrin repeat domain, preferably as described in WO 2002/020565. Examples of designed ankyrin repeat domains with binding specificity for HGF are shown in the Examples.

In a further embodiment, the invention relates to a recombinant binding protein comprising at least one ankyrin repeat domain with binding specificity for a mammalian HGF, wherein the ankyrin repeat domain inhibits the binding of HGF to c-Met in PBS with an $IC_{50}$ value below $10^{-7}$M. Preferably, said ankyrin repeat domain inhibits the binding of HGF to c-Met in PBS with an $IC_{50}$ value below $10^{-8}$M, more preferably below $10^{-9}$M, $10^{-10}$M, or most preferably below $10^{-11}$M.

The half maximal inhibitory concentration ($IC_{50}$) is a measure of the effectiveness of a compound, such as a binding domain of the invention, in inhibiting a biological, biochemical or biophysical function. Methods to determine $IC_{50}$ values of inhibition of protein-protein interactions, such as competition ELISAs are well known to the person skilled in the art. The measured $IC_{50}$ values of a particular inhibitor of a protein-protein interaction can vary if measured under different conditions (e.g., salt concentration, pH). Thus, measurements of $IC_{50}$ values are preferably made with standardized solutions of protein and a standardized buffer, such as PBS.

Example 5 shows how such $IC_{50}$ values of such ankyrin repeat inhibiting the inhibiting the binding of HGF to c-Met can be determined and recombinant binding proteins comprising an ankyrin repeat domain inhibiting the binding of HGF to c-Met in PBS with an $IC_{50}$ value below $10^{-7}$M.

In a further embodiment, the invention relates to a recombinant binding protein comprising at least one ankyrin repeat domain with binding specificity for HGF, which inhibits the HGF stimulated phosphorylation of c-Met in A549 cells (ATCC, cat number: CCL-185). A549 cells were starved for 24 hours and stimulated with HGF in the presence of a titration of an ankyrin repeat domain with specificity for HGF. Assessment of the ability of the compounds of the invention to inhibit HGF stimulated cMet phosphorylation in A549 cells was measured by standard means well known to the person skilled in the art. Example 4 shows how such $IC_{50}$ values of such ankyrin repeat domains or proteins inhibiting the phosphorylation of c-Met can be determined and shows recombinant binding proteins comprising an ankyrin repeat domain inhibiting the phosphorylation of c-Met in A549 cells with an $IC_{50}$ value below $10^{-7}$M Preferably, said repeat domain inhibits the HGF stimulated phosphorylation of c-Met in A549 cells with an $IC_{50}$ value below $10^{-8}$M, more preferably below $10^{-9}$M, $10^{-10}$M, or most preferably $10^{-11}$M.

In a further embodiment, the invention relates to a recombinant binding protein comprising at least one ankyrin repeat domain with binding specificity for HGF, which inhibits the HGF stimulated proliferation of U87 cells (ATCC, cat number: HTB-14) with an $IC_{50}$ value below $10^{-6}$M. Preferably, said repeat domain inhibits the HGF stimulated proliferation of U87 cells with an $IC_{50}$ value below $10^{-7}$M, more preferably below $10^{-8}$M, $10^{-9}$M, $10^{-10}$M, or most preferably $10^{-11}$M.

U87 cells are responsive to HGF for growth and as such can be used to measure the functional inhibitory capability of the compounds of the invention. U87 cells are grown in culture medium and seeded in DMEM containing 1% FBS (assay medium). Cells are cultured for 24 h prior to addition of HGF and a titration of the anti-HGF DARPin. Assessment of the ability of the compounds of the invention to inhibit HGF is determined by the proliferative capacity of the U87 cells as measured by standard measurements well known to the person skilled in the art. Example 4 shows how such $IC_{50}$ values of such ankyrin repeat proteins inhibiting the proliferation of U87 cells can be determined and recombinant binding proteins comprising an ankyrin repeat domain inhibiting the HGF stimulated proliferation of U87 cells with an $IC_{50}$ value below $10^{-6}$M.

The invention relates to a recombinant binding protein comprising at least one ankyrin repeat domain with binding specificity for HGF, wherein said binding protein and/or ankyrin repeat domain has a midpoint denaturation temperature (Tm) above 40° C. upon thermal unfolding in PBS and forms less than 5% (w/w) insoluble aggregates at concentrations up to 10 g/L when incubated at 37° C. for 1 day in PBS.

The term "PBS" means a phosphate buffered water solution containing 137 mM NaCl, 10 mM phosphate and 2.7 mM KCl and having a pH of 7.4.

Preferably, the recombinant binding protein and/or binding domain has a midpoint denaturation temperature (Tm) above 45° C., more preferably above 50° C., more preferably above 55° C., and most preferably above 60° C. upon thermal unfolding in PBS at pH 7.4. A binding protein or a binding domain of the invention possesses a defined secondary and tertiary structure under physiological conditions. Thermal unfolding of such a polypeptide results in a loss of its tertiary and secondary structure, which can be followed, for example, by circular dichroism (CD) measurements. The midpoint denaturation temperature of a binding protein or binding domain upon thermal unfolding corresponds to the temperature at the midpoint of the cooperative transition in physiological buffer upon heat denaturation of said protein or domain by slowly increasing the temperature from 10° C. to about 100° C. The determination of a midpoint denaturation temperature upon thermal unfolding is well known to the person skilled in the art. This midpoint denaturation temperature of a binding protein or binding domain upon thermal unfolding is indicative of the thermal stability of said polypeptide.

Also preferred is a recombinant binding protein and/or ankyrin repeat domain forming less than 5% (w/w) insoluble aggregates at concentrations up to 20 g/L, preferably up 40 g/L, more preferably up to 60 g/L, even more preferably up to 80 g/L, and most preferably up to 100 g/L when incubated for over 5 days, preferably over 10 days, more preferably over 20 days, more preferably over 40 days, and most preferably over 100 days at 37° C. in PBS. The formation of insoluble aggregates can be detected by the appearance of visual precipitations, gel filtration or dynamic light scattering, which strongly increases upon formation of insoluble aggregates. Insoluble aggregates can be removed from a protein sample by centrifugation at 10,000×g for 10 minutes. Preferably, a recombinant binding protein and/or ankyrin repeat domain forms less than 2%, more preferably less than 1%, 0.5%, 0.2%, 0.1%, or most preferably less than 0.05% (w/w) insoluble aggregates under the mentioned incubation conditions at 37° C. in PBS. Percentages of insoluble aggregates can be determined by separation of the insoluble aggregates from soluble protein, followed by determination of the protein amounts in the soluble and insoluble fraction by standard quantification methods.

Also preferred is a recombinant binding protein and/or ankyrin repeat domain that does not lose its native three-dimensional structure upon incubation in PBS containing 100 mM dithiothreitol (DTT) for 1 or 10 hours at 37° C.

In one particular embodiment the invention relates to a recombinant binding protein comprising an ankyrin repeat domain, specifically binding to HGF and having the indicated or preferred midpoint denaturation temperature and non-aggregating properties as defined above.

In a further embodiment, the invention relates to a recombinant binding protein comprising at least one ankyrin repeat domain with binding specificity for a mammalian HGF, wherein the ankyrin repeat domain competes for binding to a mammalian HGF with an ankyrin repeat domain selected from the group consisting of SEQ ID NOs: 33 to 61; preferably SEQ ID NOs: 33, 37, 41, 42, 43, 48, 51, 52, 57, 58, 59, 60 and 61; more preferably, 37, 42, 43, 51, 52 and 60; even more preferably, 37, 43, 51 and 60, in particular SEQ ID NO:51 and 60.

Also preferably said ankyrin repeat domain competes for binding to a mammalian HGF with a binding protein selected from the group of DARPins #33 to 61. Preferably, said repeat domain competes for binding to a mammalian HGF with a binding protein from the group of DARPins #24, 45 and 50. More preferably, said ankyrin repeat domain competes for binding to a mammalian HGF with binding protein DARPin #24 or 50.

The term "compete for binding" means the inability of two different binding domains of the invention to bind simultaneously to the same target, while both are able to bind the same target individually. Thus, such two binding domains compete for binding to said target.

Preferably, said two competing binding domains bind to an overlapping or the same binding epitope on said target. Methods, such as competition Enzyme-Linked Immuno Sorbent Assay (ELISA) or competition SPR measurements (e.g. by using the Proteon instrument from BioRad), to determine if two binding domains compete for binding to a target, are well known to the practitioner in the art. An example of such an competition SPR measurement is shown in Example 2.

In a further embodiment, the invention relates to a recombinant binding protein comprising at least one ankyrin repeat domain with binding specificity for a mammalian HGF, wherein said ankyrin repeat domain comprises an amino acid sequence that has at least 70% amino acid sequence identity with one ankyrin repeat domain selected from the group consisting of SEQ ID NOs: 33 to 61,
wherein G at position 1 and/or S at position 2 of said ankyrin repeat domain are optionally missing; and
L at the second last position and/or N at the last position of said ankyrin repeat domain are optionally exchanged by A.

Preferably, such an ankyrin repeat domain in a recombinant binding protein of the invention comprises an amino acid sequence that has at least 70% amino acid sequence identity with one ankyrin repeat domain selected from the group consisting of SEQ ID NOs: 33, 37, 41, 42, 43, 48, 51, 52, 57, 58, 59, 60 and 61; more preferably, 37, 42, 43, 51, 52 and 60; even more preferably, 37, 43, 51 and 60, in particular SEQ ID NO:51 and 60.

Preferably, such an ankyrin repeat domain in a recombinant binding protein of the invention comprises an amino acid sequence with at least 70% amino acid sequence identity with one, two or three ankyrin repeat modules present between the N-terminal and C-terminal capping modules of an ankyrin repeat domain selected from the group consisting of SEQ ID NOs: 33 to 61.

Preferably, such an ankyrin repeat domain or such one, two or three repeat modules comprises an amino acid sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity.

Preferably, up to 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 amino acids in the repeat domains SEQ ID NO:33 to 61 are exchanged by another amino acid.

Preferably, when amino acids are exchanged in the capping modules of SEQ ID NO: 1 to 8, the repeat modules of SEQ ID NO:12 to 25 or the repeat domains of SEQ ID NO:33 to 61, these amino acids are selected from the group consisting of A, D, E, F, H, I, K, L, M, N, Q, R, S, T, V, W and Y; more preferably from the group consisting of A, D, E, H, I, K, L, Q, R, S, T, V, and Y. Also preferably, an amino acid is exchanged by a homologous amino acid; i.e. an amino acid is exchanged by an amino acid having a side chain with similar biophysical properties. For example, the negative charged amino acid D may be replaced by the negative charged amino acid E, or a hydrophobic amino acid such as L may be replaced by A, I or V. The techniques of exchanging an amino acid by another amino acid in a polypeptide are well known to the person skilled in the art.

In a further embodiment, the invention relates to a recombinant binding protein comprising at least one ankyrin repeat domain with binding specificity for a mammalian HGF, wherein said ankyrin repeat domain is selected from the group consisting of SEQ ID NOs: 33 to 61,
wherein G at position 1 and/or S at position 2 of said ankyrin repeat domain are optionally missing, and
L at the second last position and/or N at the last position of said ankyrin repeat domain are optionally exchanged by A.

Preferably, such an ankyrin repeat domain is selected from the group consisting of SEQ ID NO: 33, 37, 41, 42, 43, 48, 51, 52, 57, 58, 59, 60 and 61; more preferably, 37, 42, 43, 51, 52 and 60; even more preferably, 37, 43, 51 and 60, in particular SEQ ID NO:51 and 60.

In a further embodiment, the invention relates to a recombinant binding protein comprising at least one ankyrin repeat domain with binding specificity for a mammalian HGF, wherein said ankyrin repeat domain comprises an ankyrin repeat module having an amino acid sequence selected from the group consisting of SEQ ID NO:12 to 25 and sequences in which up to 9 amino acids in SEQ ID NO:12 to 25 are exchanged by any amino acid.

Preferably, such a recombinant binding protein comprises at least an ankyrin repeat module having an amino acid sequence selected from the group consisting of SEQ ID NO: 12 to 25 and sequences in which up to 9 amino acids in SEQ ID NO: 12 to 25 are exchanged by any amino acid, and of which up to 6; preferably, 5; more preferably, 4; more preferably, 3; more preferably, 2; most preferably, 1 of said 9 amino acid exchanges are located in positions 1, 3, 4, 6, 14, and/or 15 of SEQ ID NOs: 12 to 25.

Preferably, such an ankyrin repeat module of said ankyrin repeat domain is selected from the group consisting of SEQ ID NO: 12, 15, 19, 21 and 24; more preferably, 19 and 21.

More preferably, such an ankyrin repeat module of said ankyrin repeat domain is selected from the group consisting of SEQ ID NO: 12, 13, 14, 15, 18, 19, 20, 21, and 22; even more preferably, 12, 15, 18, 19, 20, 21 and 24; more preferably, 18, 19, 20, and 21.

Preferably, up to 8 amino acids in the repeat modules of SEQ ID NO:12 to 25 are exchanged by another amino acid, more preferably up to 7 amino acids, more preferably up to 6 amino acids, more preferably up to 5 amino acids, even more preferably up to 4 amino acids, more preferably up to 3 amino acids, more preferably up to 2 amino acids, and most preferably 1 amino acid.

In a further embodiment, the invention relates to a recombinant binding protein, wherein the ankyrin repeat domain with binding specificity to HGF comprises a repeat module with the ankyrin repeat sequence KDRYGDTPLHLAA-DIGHLEIVEVLLKAGADVNA (SEQ ID NO:18) and sequences in which up to 9 amino acids in SEQ ID NO:18 are exchanged by any amino acid and wherein
K at position 1 is optionally exchanged by Q, H, N, I, T, Y, V, F, D, R, L or S; preferably by Q, H, N, I, T, Y, V or F; also preferably by Q, H, I, T, Y, V; most preferably by Q or H;
R at position 3 is optionally exchanged by A, T, K, H, N, Y, F, S or D; preferably by A, T, K, H or N; most preferably by A;
Y at position 4 is optionally exchanged by F, W, R, L, S or T; preferably by F or W;
D at position 6 is optionally exchanged by L, A, N, E, S T; preferably by L or A;
D at position 14 is optionally exchanged by S, N, M, T, F; preferably by S or N;
I at position 15 is optionally exchanged by Y, A, N, T, R, V, K, D, L, S; preferably by Y, A, N, T, R or V; most preferably by Y or A; and
E at position 19 is optionally exchanged by K.

Preferred is a recombinant binding protein, wherein the ankyrin repeat domain with binding specificity to HGF comprises a repeat module with the ankyrin repeat sequence KDRYGDTPLHLAADIGHLEIVEVLLKAGADVNA
(SEQ ID NO:18) and sequences in which up to 9 amino acids in SEQ ID NO:18 are exchanged by any amino acid and wherein
K at position 1 is optionally exchanged by Q, H, I, V
R at position 3 is optionally exchanged by A, T or N; preferably by A;
Y at position 4 is optionally exchanged by F or W;
D at position 6 is optionally exchanged by N;
D at position 14 is optionally exchanged by S;
I at position 15 is optionally exchanged by Y or A; and
E at position 19 is optionally exchanged by K.

In a further embodiment, the invention relates to a recombinant binding protein, wherein the ankyrin repeat domain with binding specificity to HGF comprises a repeat module with the ankyrin repeat sequence EDYFGNTPLH-LAASYGHLEIVEVLLKAGADVNA (SEQ ID NO:19) and sequences in which up to 9 amino acids in SEQ ID NO:19 are exchanged by any amino acid and wherein
E at position 1 is optionally exchanged by D, H, N, F, A, L, Q, I; preferably by D, H, N; most preferably by D or H;
Y at position 3 is optionally exchanged by W, S, H, V, F, A or D; preferably by W, S, H, V, A or F; most preferably by W or S;
F at position 4 is optionally exchanged by Y, A or W; preferably by Y or A;
N at position 6 is optionally exchanged by D, H, I or M; preferably by D or H; most preferably D;
S at position 14 is optionally exchanged by N or H; and
Y at position 15 is optionally exchanged by M, W, L, T, V, S, A, I or N; preferably by M, W, L, T, A or V; also preferably by M, A or W; most preferably by A.

Preferred is a recombinant binding protein, wherein the ankyrin repeat domain with binding specificity to HGF comprises a repeat module with the ankyrin repeat sequence EDYFGNTPLHLAASYGHLEIVEVLLKAGADVNA
(SEQ ID NO:19) and sequences in which up to 9 amino acids in SEQ ID NO:19 are exchanged by any amino acid and wherein
E at position 1 is optionally exchanged by D, F, A, or L; most preferably D, or A;
Y at position 3 is optionally exchanged by W, S, or V;
F at position 4 is optionally exchanged by Y;
N at position 6 is optionally exchanged by D;
Y at position 15 is optionally exchanged by M, L, S, or A; preferably M, A, or L; most preferably A, or L.

Preferred is a recombinant binding protein, wherein said ankyrin repeat domain comprises said ankyrin repeat module of SEQ ID NO:18 and said ankyrin repeat module of SEQ ID NO:19. Preferably, said ankyrin repeat module of SEQ ID NO:19 directly follows said ankyrin repeat module of SEQ ID NO:18 in said ankyrin repeat domain. For example, in the ankyrin repeat domain of DARPin #51 said ankyrin repeat module of SEQ ID NO:19 directly follows said ankyrin repeat module of SEQ ID NO:18.

In yet another embodiment, the invention relates to a recombinant binding protein, wherein the ankyrin repeat domain with binding specificity to HGF comprises a repeat module with the ankyrin repeat sequence KDDYGNTPLH-LAANTGHLEIVEVLLKAGADVNA (SEQ ID NO:20) and sequences in which up to 9 amino acids in SEQ ID NO:20 are exchanged by any amino acid and wherein
K at position 1 is optionally exchanged by M, I, D, L, Q, V, R, T or H; preferably by M, I or D; most preferably by I or D;
D at position 3 is optionally exchanged by H, Y, T, W or F; preferably by H or Y;
Y at position 4 is optionally exchanged by S, N, A, G, F or R; preferably by S, N, A or G; most preferably by S;
N at position 6 is optionally exchanged by S, T, L or Y; preferably by S;
N at position 14 is optionally exchanged by L, F, M or I; preferably by L or I;
T at position 15 is optionally exchanged by S, W, V, E, F or A; preferably by S;
H at position 17 is optionally exchanged by R; and
E at position 19 is optionally exchanged by K.

Preferred is a recombinant binding protein, wherein the ankyrin repeat domain with binding specificity to HGF comprises a repeat module with the ankyrin repeat sequence KDDYGNTPLHLAANTGHLEIVEVLLKAGADVNA (SEQ ID NO:20) and sequences in which up to 9 amino acids in SEQ ID NO:20 are exchanged by any amino acid and wherein
K at position 1 is optionally exchanged by M, D, L, Q, or V;
D at position 3 is optionally exchanged by Y, or T;
Y at position 4 is optionally exchanged A, or N;
T at position 15 is optionally exchanged by S;
H at position 17 is optionally exchanged by R; and
E at position 19 is optionally exchanged by K.

Also preferred is a recombinant binding protein, wherein said ankyrin repeat domain comprises said ankyrin repeat module of SEQ ID NO:19 and said ankyrin repeat module of SEQ ID NO:20. Preferably, said ankyrin repeat module of SEQ ID NO:20 directly follows said ankyrin repeat module of SEQ ID NO:19 in said ankyrin repeat domain. For example, in the ankyrin repeat domain of DARPin #51 said ankyrin repeat module of SEQ ID NO:20 directly follows said ankyrin repeat module of SEQ ID NO:19.

Also preferred is a recombinant binding protein, wherein said ankyrin repeat domain comprises said ankyrin repeat module of SEQ ID NO:18, said ankyrin repeat module of SEQ ID NO:19 and said ankyrin repeat module of SEQ ID NO:20. Preferably, said ankyrin repeat module of SEQ ID NO:19 directly follows said ankyrin repeat module of SEQ ID NO:18 in said ankyrin repeat domain and said ankyrin repeat module of SEQ ID NO:20 directly follows said ankyrin repeat module of SEQ ID NO:19 in said ankyrin repeat domain. For example, in the ankyrin repeat domain of DARPin #51 said ankyrin repeat module of SEQ ID NO:20 directly follows said ankyrin repeat module of SEQ ID NO:19, which directly follows said ankyrin repeat module of SEQ ID NO:18.

In yet another embodiment, the invention relates to a recombinant binding protein, wherein the ankyrin repeat domain with binding specificity to HGF comprises a repeat module with the ankyrin repeat sequence HDYSGFTPLH-LAAYYGHLEIVEVLLKHGADVNA (SEQ ID NO:12) and sequences in which up to 9 amino acids in SEQ ID NO:12 are exchanged by any amino acid and wherein
H at position 1 is optionally exchanged by T, S, N, Q, I, K, F, Y or V; preferably by T, S, N, Q or I; most preferably by T or S;
Y at position 3 is optionally exchanged by R, N, D, M, W, E, A, Q or L; preferably by R, N or D; most preferably by R or N;
S at position 4 is optionally exchanged by N, T or W; preferably by N or T;
F at position 6 is optionally exchanged by I;
Y at position 14 is optionally exchanged by F;
Y at position 15 is optionally exchanged by W or H; and
I at position 20 is optionally exchanged by V or L.

In yet another embodiment, the invention relates to a recombinant binding protein, wherein the ankyrin repeat domain with binding specificity to HGF comprises a C-terminal capping module with the sequence FDDWGHTPLH-LAARYGHLEIVEVLLKYGADVNA (SEQ ID NO:13) and sequences in which up to 9 amino acids in SEQ ID NO:13 are exchanged by any amino acid and wherein
F at position 1 is optionally exchanged by T, H, L, D, Y, K or E; preferably by T, H, L or D; most preferably by T or H;
D at position 3 is optionally exchanged by R, K, A, N, Y, S, L, T or F; preferably by R, K, A or N; most preferably by A, R or K;
W at position 4 is optionally exchanged by F, Y or R; preferably by F;
H at position 6 is optionally exchanged by L, I, M, N or K; preferably by L or I;
R at position 14 is optionally exchanged by H, Y, S, F, A, N or I; preferably by H, Y or S; most preferably by H; and
Y at position 15 is optionally exchanged by F, L, T, K or R; preferably by F, L or T; most preferably by F.

Preferred is a recombinant binding protein, wherein said ankyrin repeat domain comprises said ankyrin repeat module of SEQ ID NO:12 and said ankyrin repeat module of SEQ ID NO:13. Preferably, said ankyrin repeat module of SEQ ID NO:13 directly follows said ankyrin repeat module of SEQ ID NO:12 in said ankyrin repeat domain. For example, in the ankyrin repeat domain of DARPin #33 said ankyrin repeat module of SEQ ID NO:13 directly follows said ankyrin repeat module of SEQ ID NO:12.

In yet another embodiment, the invention relates to a recombinant binding protein, wherein the ankyrin repeat domain with binding specificity to HGF comprises a C-terminal capping module with the sequence KYEDGLTPLH-LAAFYGHLEIVEVLLRHGADVNA (SEQ ID NO:15) and sequences in which up to 9 amino acids in SEQ ID NO:15 are exchanged by any amino acid and wherein
A at position 13 is optionally exchanged by V; and
R at position 26 is optionally exchanged by K.

In yet another embodiment, the invention relates to a recombinant binding protein, wherein the ankyrin repeat domain with binding specificity to HGF comprises a C-terminal capping module with the sequence TDAWGHTPLH-LAAYLGHLEIVEVLLKYGADVNA (SEQ ID NO:16) and sequences in which up to 9 amino acids in SEQ ID NO:16 are exchanged by any amino acid and wherein
P at position 8 is optionally exchanged by T;
A at position 12 is optionally exchanged by T;
Y at position 14 is optionally exchanged by S, H or A; preferably by S or H
L at position 15 is optionally exchanged by Y, N or S; preferably by Y or N; and
A at position 33 is optionally exchanged by T.

Preferred is a recombinant binding protein, wherein said ankyrin repeat domain comprises said ankyrin repeat module of SEQ ID NO:15 and said ankyrin repeat module of SEQ ID NO:16. Preferably, said ankyrin repeat module of SEQ ID NO:16 directly follows said ankyrin repeat module of SEQ ID NO:15 in said ankyrin repeat domain. For example, in the ankyrin repeat domain of DARPin #41 said ankyrin repeat module of SEQ ID NO:16 directly follows said ankyrin repeat module of SEQ ID NO:15.

In yet another embodiment, the invention relates to a recombinant binding protein, wherein the ankyrin repeat domain with binding specificity to HGF comprises a repeat module with the ankyrin repeat sequence HDTWGLTPLH-LAAFHGHQEIVEVLLKHGADVNA (SEQ ID NO:21) and sequences in which up to 9 amino acids in SEQ ID NO:21 are exchanged by any amino acid.

In yet another embodiment, the invention relates to a recombinant binding protein, wherein the ankyrin repeat domain with binding specificity to HGF comprises a repeat module with the ankyrin repeat sequence QDFYGKTPLH-LAALRGHLEIVEVLLKYGADVNA (SEQ ID NO:22) and sequences in which up to 9 amino acids in SEQ ID NO:22 are exchanged by any amino.

Preferred is a recombinant binding protein, wherein said ankyrin repeat domain comprises said ankyrin repeat module of SEQ ID NO:21 and said ankyrin repeat module of SEQ ID NO:22. Preferably, said ankyrin repeat module of SEQ ID NO:22 directly follows said ankyrin repeat module of SEQ ID NO:21 in said ankyrin repeat domain. For example, in the ankyrin repeat domain of DARPin #60 said ankyrin repeat module of SEQ ID NO:22 directly follows said ankyrin repeat module of SEQ ID NO:21.

In yet another embodiment, the invention relates to a recombinant binding protein, wherein the ankyrin repeat domain with binding specificity to HGF comprises a repeat module with the ankyrin repeat sequence HDYLGLTPLH-LAASDGHLEIVEVLLKHGADVNA (SEQ ID NO:23) and sequences in which up to 9 amino acids in SEQ ID NO:23 are exchanged by any amino acid and wherein
H at position 1 is optionally exchanged by N, L, K, R, F, Q or D; preferably by N, L or K; most preferably by N;
Y at position 3 is optionally exchanged by F, Q, T, R, N, S or D; preferably by F, Q or T; most preferably by F or Q;
L at position 4 is optionally exchanged by V, T, Q, Y, D or F; preferably by V or T;
L at position 6 is optionally exchanged by D;
S at position 14 is optionally exchanged by A, N or F; preferably by A or N; and
D at position 15 is optionally exchanged by I, T, S, R, A, Y or M; preferably by I, T, S or R; most preferably I or T.

In yet another embodiment, the invention relates to a recombinant binding protein, wherein the ankyrin repeat domain with binding specificity to HGF comprises a repeat module with the ankyrin repeat sequence YDYNGLTPLH-LAANNGHLEIVEVLLKYGADVNA (SEQ ID NO:24) and sequences in which up to 9 amino acids in SEQ ID NO:24 are exchanged by any amino acid and wherein
Y at position 1 is optionally exchanged by S, I, T, Q, E, M, K, D or V; preferably by S, I or T; most preferably by S or I;
Y at position 3 is optionally exchanged by A, F, V, M, W, T, R or Q; preferably by A, F, V or M; most preferably by A or V;
N at position 4 is optionally exchanged by Y, F, T or W; preferably by Y;
L at position 6 is optionally exchanged by F, H, Y, N or W; preferably by F, H, Y or N; most preferably by F or H;
H at position 10 is optionally exchanged by Y;
A at position 12 is optionally exchanged by T or V;
N at position 14 is optionally exchanged by S;
N at position 15 is optionally exchanged by V, M or T; preferably V; and
I at position 20 is optionally exchanged by V or L.

In yet another embodiment, the invention relates to a recombinant binding protein, wherein the ankyrin repeat domain with binding specificity to HGF comprises a repeat module with the ankyrin repeat sequence FDVAGYTPLH-LAAYFGHLEIVEVLLKYGADVNA (SEQ ID NO:25) and sequences in which up to 9 amino acids in SEQ ID NO:25 are exchanged by any amino acid and wherein
F at position 1 is optionally exchanged by I, M, T, D, Y, Q, E, H, A or S; preferably by I, M, T, D, Y or Q; also preferably I, T, D or Y; most preferably by I or Y;
V at position 3 is optionally exchanged by I, H, S, A, D, or W; preferably I, H or S; most preferably by I or S;
A at position 4 is optionally exchanged by F, Y, V, M, N, L, T, H or I; preferably by F, Y, V or M; most preferably by F or Y;
Y at position 6 is optionally exchanged by F, H, T, W, M, N, Q or S; preferably by F, H, T or W; most preferably by F or T;
Y at position 14 is optionally exchanged by H, M, L, N, I, R, W or T; preferably by H, L, N, I, R or T; most preferably by H or L; and
F at position 15 is optionally exchanged by Y, H, M, T, V, L, N or I; preferably Y, H, T or V; most preferably T or V.

Preferred is a recombinant binding protein, wherein said ankyrin repeat domain comprises said ankyrin repeat module of SEQ ID NO:23 and said ankyrin repeat module of SEQ ID NO:24. Preferably, said ankyrin repeat module of SEQ ID NO:24 directly follows said ankyrin repeat module of SEQ ID NO:23 in said ankyrin repeat domain. For example, in the ankyrin repeat domain of DARPin #57 said ankyrin repeat module of SEQ ID NO:24 directly follows said ankyrin repeat module of SEQ ID NO:23.

Also preferred is a recombinant binding protein, wherein said ankyrin repeat domain comprises said ankyrin repeat module of SEQ ID NO:24 and said ankyrin repeat module of SEQ ID NO:25. Preferably, said ankyrin repeat module of SEQ ID NO:25 directly follows said ankyrin repeat module of SEQ ID NO:24 in said ankyrin repeat domain. For example, in the ankyrin repeat domain of DARPin #57 said ankyrin repeat module of SEQ ID NO:25 directly follows said ankyrin repeat module of SEQ ID NO:24.

Also preferred is a recombinant binding protein, wherein said ankyrin repeat domain comprises said ankyrin repeat module of SEQ ID NO:23, said ankyrin repeat module of SEQ ID NO:24 and said ankyrin repeat module of SEQ ID NO:25. Preferably, said ankyrin repeat module of SEQ ID NO:24 directly follows said ankyrin repeat module of SEQ ID NO:23 in said ankyrin repeat domain and said ankyrin repeat module of SEQ ID NO:25 directly follows said ankyrin repeat module of SEQ ID NO:24 in said ankyrin repeat domain. For example, in the ankyrin repeat domain of DARPin #57 said ankyrin repeat module of SEQ ID NO:25 directly follows said ankyrin repeat module of SEQ ID NO:24, which directly follows said ankyrin repeat module of SEQ ID NO:23.

Further preferred is a N-terminal or C-terminal ankyrin capping module comprising an N-terminal or C-terminal ankyrin capping repeat, respectively, wherein one or more of the amino acids residues in said capping repeat are replaced by an amino acid residue found at the corresponding position on alignment of a corresponding ankyrin capping unit or ankyrin repeat unit.

The replacement of amino acids can be by any of the 20 most often naturally occurring amino acids, preferably by amino acids selected from the group consisting of A, D, E, F, H, I, K, L, M, N, Q, R, S, T, V, W and Y; and more preferably from the group consisting of A, D, E, H, I, K, L, Q, R, S, T, V, and Y. Also preferably, the replacement of amino acids is by a homologous amino acid; i.e. an amino acid is replaced by an amino acid having a side chain with similar biophysical properties. For example, the negative charged amino acid D may be replaced by the negative charged amino acid E, or a hydrophobic amino acid such as L may be replaced by A, I or V. The replacement of an amino acid by a homologous amino acid is well known to the person skilled in the art.

Also preferred is a C-terminal ankyrin capping module comprising the amino acid A at position 27 and 28 of any of the above C-terminal capping modules based on SEQ ID NO:4 to 8.

Also preferred is a C-terminal capping module comprising the amino acids from position 1 to 26 or from position 1 to 27 of any of the above C-terminal capping modules based on SEQ ID NO:4 to 8.

Amino acids G at position 1 and/or S at position 2 of SEQ ID NO:1 to 3 can be removed from N-terminal ankyrin capping modules without any apparent influence on the properties. These two amino acids serve as linkers to connect the ankyrin repeat domain to further amino acids and proteins. The invention also comprises such ankyrin repeat domains comprising N-terminal ankyrin capping modules wherein G at position 1 and/or S at position 2 are removed. It is understood that the amino acid positions (e.g. "position 33") in an ankyrin repeat domain as defined herein are adapted accordingly, resulting in a number shift, e.g. "position 33" will become "position 32", if one amino acid is missing, or "position 33" will become "position 31", if two amino acid are missing.

An ankyrin capping module of an ankyrin repeat domain of the invention can be exchanged by an ankyrin capping module by combining techniques, such as alignment of amino acid sequences, mutagenesis and gene synthesis, known to the person skilled in the art. For example, the C-terminal capping repeat of SEQ ID NO:33 can be replaced by the C-terminal capping repeat of SEQ ID NO:8 by (i) determination of the C-terminal capping repeat of SEQ ID NO:33 (i.e. sequence position 132 to 159) by sequence alignment with SEQ ID NO:8, (ii) replacing the sequence of the determined C-terminal capping repeat of SEQ ID NO:33 with the sequence of SEQ ID NO:8, (iii) generation of a gene encoding the repeat domain encoding the exchanged C-terminal capping module, (iv) expressing of the modified repeat domain in the cytoplasm of E. coli and (v) purification of the modified repeat domain by standard means. As a further example, the N-terminal capping repeat of SEQ ID NO:33 can be replaced by the N-terminal capping repeat of SEQ ID NO:2 by (i) determination of the N-terminal capping repeat of SEQ ID NO:33 (i.e. sequence position 1 to 32) by sequence alignment with SEQ ID NO:2, (ii) replacing the sequence of the determined N-terminal capping repeat of SEQ ID NO:33 with the sequence of SEQ ID NO:2, (iii) generation of a gene encoding the repeat domain encoding the exchanged N-terminal capping module, (iv) expressing of the modified repeat domain in the cytoplasm of E. coli and (v) purification of the modified repeat domain by standard means.

Furthermore, an ankyrin repeat domain of the invention can be constructed genetically by assembling a N-terminal ankyrin capping module (e.g. the N-terminal capping repeat of SEQ ID NO:2) followed by one or more repeat modules (e.g. the three ankyrin repeat modules comprising the amino acid residues from position 33 to 131 of SEQ ID NO:33) and a C-terminal capping module (e.g. the C-terminal capping repeat of SEQ ID NO:8) by means of gene synthesis. The genetically assembled repeat domain gene can then be expressed in E. coli as described herein.

Further preferred is a recombinant binding protein, repeat domain, repeat module, N-terminal capping module or C-terminal capping module having an amino acid sequence devoid of amino acids C, M or N.

Further preferred is a recombinant binding protein, repeat domain, repeat module, N-terminal capping module or C-terminal capping module having an amino acid sequence devoid of amino acid D, E or N followed by G.

Further preferred is a recombinant binding protein or repeat domain comprising any such N-terminal or C-terminal capping module.

In a further preferred embodiment of a recombinant binding protein comprising an ankyrin repeat domain according to the present invention, one or more of the amino acid residues of the N-terminal capping module of said repeat domain is exchanged by an amino acid residue found at the corresponding position on alignment of an N-terminal capping unit. Preferably, up to 30% of the amino acid residues are exchanged, more preferably, up to 20%, and even more preferably, up to 10% of the amino acid residues are exchanged. Most preferably, such an N-terminal capping unit is a naturally occurring N-terminal capping unit.

In a further preferred embodiment of a recombinant binding protein comprising an ankyrin repeat domain according to the present invention, one or more of the amino acid residues of the C-terminal capping module of said repeat domain is exchanged by an amino acid residue found at the corresponding position on alignment of a C-terminal capping unit. Preferably, up to 30% of the amino acid residues are exchanged, more preferably, up to 20%, and even more preferably, up to 10% of the amino acid residues are exchanged. Most preferably, such a C-terminal capping unit is a naturally occurring C-terminal capping unit.

In still another particular embodiment, up to 30, 29, 28, 27, 26, 25, 24, 23, 22, 21, 20, 19, 18, 17, 16, 15, 14, 13, 13, 12, 11, 10, 9, 8, 7, 6, 5, 4, 3, 2 or 1% of the amino acid residues are exchanged with amino acids which are not found in the corresponding positions of repeat units, N-terminal capping units or C-terminal capping units.

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

Further preferred are non-naturally occurring capping modules, repeat modules, binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

In one particular embodiment the invention relates to a recombinant binding protein comprising an ankyrin repeat domain specifically binding to HGF and further comprising an ankyrin repeat domain specifically binding to vascular endothelial growth factors A (VEGF-A). Examples of ankyrin repeat domains with specificity for HGF are given herein and examples of ankyrin repeat domains with specificity to VEGF-A are described in WO 2010/060748 or WO 2011/135067. Also preferably, such a recombinant binding protein further comprises one ore more, preferably one or two, ankyrin repeat domains with specificity for human serum albumin. Examples of ankyrin repeat domains with specificity to human serum albumin are described in WO 2012/069654. Any such repeat domains with specificities for serum albumin, VEGF-A or HGF can be linked by polypeptide linkers (e.g. SEQ ID NO:10 or 11) by genetic means by methods known to the person skilled in the art.

Another preferred embodiment is a recombinant binding protein comprising an ankyrin repeat domain with binding specificity for HGF comprising one, two, three or more internal repeat modules that will participate in binding to HGF. Preferably, such an ankyrin repeat domain comprises an N-terminal capping module, two to four internal repeat modules, and a C-terminal capping module. Preferably, said capping modules are capping repeats. Also preferably, said capping modules will participate in binding to HGF.

Further preferred is a recombinant binding protein comprising two or more of said ankyrin repeat domains with binding specificity for HGF. Preferably, said binding protein comprises 2 or 3 of said repeat domains. Said two or more repeat domains have the same or different amino acid sequence.

In a further preferred embodiment of a recombinant binding protein comprising an ankyrin repeat domain according to the present invention, one or more of the amino acid residues of the repeat modules of said ankyrin repeat domain are exchanged by an amino acid residue found at the corresponding position on alignment of a repeat unit. Preferably, up to 30% of the amino acid residues are exchanged, more preferably, up to 20%, and even more preferably, up to 10% of the amino acid residues are exchanged. Most preferably, such a repeat unit is a naturally occurring repeat unit.

In still another particular embodiment, up to 30% of the amino acid residues, more preferably, up to 20%, and even more preferably, up to 10% of the amino acid residues are exchanged with amino acids which are not found in the corresponding positions of repeat units.

In further embodiments, any of the recombinant HGF binding proteins or domains described herein may be covalently bound to one or more additional moieties, including, for example, a moiety that binds to a different target to create a dual-specificity binding agent, a bioactive compound, a labeling moiety (e.g. a fluorescent label such as fluorescein, or a radioactive tracer), a moiety that facilitates protein purification (e.g. a small peptide tag, such as a His- or strep-tag), a moiety that provides effector functions for improved therapeutic efficacy (e.g. the Fc part of an antibody to provide antibody-dependent cell-mediated cytotoxicity, a toxic protein moiety such as *Pseudomonas aeruginosa* exotoxin A (ETA) or a small molecular toxic agent such as maytansinoids or DNA alkylating agents) or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein between the concentration shortly after administration and the concentration shortly before the next administration). Moieties that tend to slow clearance of a protein from the blood include hydroxyethyl starch (HES), polyethylene glycol (PEG), sugars (e.g. sialic acid), well-tolerated protein moieties (e.g. Fc fragments or serum albumin), and binding domains or peptides with specificity and affinity for abundant serum proteins, such as antibody Fc fragments or serum albumin. Examples of such binding domains with affinity for serum albumin are provided in WO 2012/069654. The recombinant binding protein of the invention may be attached to a moiety that reduces the clearance rate of polypeptides in a mammal (e.g. in mouse, rat, or human) by greater than three-fold relative to the unmodified polypeptides.

In a further embodiment, the invention relates to nucleic acid molecules encoding the particular recombinant binding proteins, the particular ankyrin repeat domains, the particular ankyrin repeat modules and the particular capping modules. Further, a vector comprising said nucleic acid molecule is considered.

Further, a pharmaceutical composition comprising one or more of the above mentioned recombinant binding proteins, in particular binding proteins comprising repeat domains, or nucleic acid molecules encoding the particular binding proteins, and optionally a pharmaceutical acceptable carrier and/or diluent is considered. Pharmaceutical acceptable carriers and/or diluents are known to the person skilled in the art and are explained in more detail below. Even further, a diagnostic composition comprising one or more of the above mentioned recombinant binding proteins, in particular binding proteins comprising repeat domains, is considered.

A pharmaceutical composition comprises recombinant binding proteins as described above and a pharmaceutically acceptable carrier, excipient or stabilizer, for example as described in Remington's Pharmaceutical Sciences 16$^{th}$ edition, Osol, A. Ed. [1980]. Suitable carriers, excipients or stabilizers known to the skilled man are saline, Ringers solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent.

The formulations to be used for in vivo administration must be aseptic or sterile. This is readily accomplished by filtration through sterile filtration membranes.

The pharmaceutical composition may be administered by any suitable method within the knowledge of the person skilled in the art.

Further, any of the above mentioned pharmaceutical composition is considered for the treatment of a disorder.

The invention further provides methods of treatment. The method comprises administering, to a patient in need thereof, a therapeutically effective amount of a recombinant binding protein of the invention.

Further, a method of treating a pathological condition in a mammal including man, comprising administering to a patient in need thereof an effective amount of the above mentioned pharmaceutical composition is considered.

Examples of such pathological conditions are atherosclerosis, restenosis, pulmonary hypertension, inflammatory joint diseases, ocular and retinal diseases and fibrotic diseases, including pulmonary fibrosis, liver cirrhosis and other disorders of the liver, scleroderma, glomerulosclerosis and cardiac fibrosis. In addition, anti-HGF therapy is useful for oncology pathological conditions, such as solid and hematological tumors. For example, gliomas, sarcomas, osteogenic sarcomas, multiple myeloma, leukemias, lymphomas and epithelial cancers, including bone metastases.

The recombinant binding protein or ankyrin repeat domain according to the invention may be obtained and/or further evolved by several methods such as display on the surface of bacteriophages (WO 1990/002809, WO 2007/006665) or bacterial cells (WO 1993/010214), ribosomal display (WO 1998/048008), display on plasmids (WO 1993/008278) or by using covalent RNA-repeat protein hybrid constructs (WO 2000/032823), or intracellular expression and selection/screening such as by protein complementation assay (WO 1998/341120). Such methods are known to the person skilled in the art.

A library of ankyrin repeat proteins used for the selection/screening of a recombinant binding protein or ankyrin repeat domain according to the invention may be obtained according to protocols known to the person skilled in the art (WO 2002/020565, Binz, H. K., et al., J. Mol. Biol., 332, 489-503, 2003, and Binz et al., 2004, loc. cit). The use of such libraries for the selection of ankyrin repeat domains with specificity for HGF is exemplified in Example 1. Furthermore, ankyrin repeat domains of the present invention may be modularly assembled from ankyrin repeat modules according to the current invention and appropriate capping modules or capping repeats (Forrer, P., et al., FEBS letters 539, 2-6, 2003) using standard recombinant DNA technologies (e.g. WO 2002/020565, Binz et al., 2003, loc. cit. and Binz et al., 2004, loc. cit).

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.

Materials

Chemicals were purchased from Sigma-Aldrich (USA). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *E. coli* XL1-blue (Stratagene, USA) or BL21 (Novagen, USA). Recombinant human HGF was purchased Peprotech (USA, product number 100-39), and recombinant mouse HGF was purchased from RnD Systems (USA; product number 2207-HG/CF). Biotinylated HGF was obtained chemically via coupling of the biotin moiety to primary amines of the protein using standard biotinylation reagents and methods (Pierce, USA).

Cell lines were purchased from LGC/ATCC (France/USA; Cat. No: A549-CCL-185, U87MG-HTB-14). Cell culture media were from Invitrogen/Lubio (Switzerland). Fetal calf serum was from Promocell (Germany; C-37350) Assay reagent for detection of cell proliferation, Cell Proliferation ELISA, BrdU (colorimetric) (Cat. No. 1164722900) was from Roche, Switzerland. Assay reagents for detection of P-c-Met were from RnDSystems (Human Phospho-HGF R/c-MET DuoSet IC; Cat No. DYC2480-5; Sample Diluent Concentrate 2; DXC002). Human HGF for cellular assays was from Peprotech (Cat No. 100-39) and reconstituted in cell culture medium containing 10% FBS.

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

Designed Ankyrin Repeat Protein Libraries

Methods to generate designed ankyrin repeat protein libraries are described (WO 2002/020565; Binz et al. 2003, loc. cit.; Binz et al. 2004, loc. cit.). By such methods designed ankyrin repeat protein libraries having randomized ankyrin repeat modules and/or randomized capping modules can be constructed. For example, such libraries could accordingly be assembled based on a fixed N-terminal capping module (e.g. the N-terminal capping module of SEQ ID NO: 2) or a randomized N-terminal capping module according to SEQ ID NO: 29, one or more randomized repeat modules according to the sequence motif of SEQ ID NO: 26, 27 or 28, and a fixed C-terminal capping module (e.g. the C-terminal capping module of SEQ ID NO: 8) or a randomized C-terminal capping module according to SEQ ID NO: 30. Preferably, such libraries are assembled to not have the amino acids C, G, M, N (in front of a G residue) or P at randomized positions of repeat or capping modules. In addition, randomized repeat modules according to the sequence motif of SEQ ID NO: 26, 27 or 28 could be further randomized at position 10 and/or position 17; the randomized N-terminal capping module according to the sequence motif of SEQ ID NO: 29 could be further randomized at position 7 and/or position 9; and the randomized C-terminal capping modules according to the sequence motif of SEQ ID NO: 30 could be further randomized at positions 10, 11 and/or 17.

Furthermore, such randomized modules in such libraries may comprise additional polypeptide loop insertions with randomized amino acid positions. Examples of such polypeptide loop insertions are complement determining region (CDR) loop libraries of antibodies or de novo generated peptide libraries. For example, such a loop insertion could be designed using the structure of the N-terminal ankyrin repeat domain of human ribonuclease L (Tanaka, N., Nakanishi, M, Kusakabe, Y, Goto, Y., Kitade, Y, Nakamura, K. T., EMBO J. 23(30), 3929-3938, 2004) as guidance. In analogy to this ankyrin repeat domain where ten amino acids are inserted in the beta-turn present close to the boarder of two ankyrin repeats, ankyrin repeat proteins libraries may contain randomized loops (with fixed and randomized positions) of variable length (e.g. 1 to 20 amino acids) inserted in one or more beta-turns of an ankyrin repeat domain.

Any such N-terminal capping module of an ankyrin repeat protein library preferably possesses the RELLKA (SEQ ID NO:63) or RILKAA (SEQ ID NO:64) motif instead of the RILLAA motif (SEQ ID NO:65) (e.g. present from position 21 to 26 in SEQ ID NO:29) and any such C-terminal capping module of an ankyrin repeat protein library preferably possesses the KAA or KLA motif instead of the KLN motif (e.g. the last three amino acids in SEQ ID NO:30).

The design of such an ankyrin repeat protein library may be guided by known structures of an ankyrin repeat domain interacting with a target. Examples of such structures, identified by their Protein Data Bank (PDB) unique accession or identification codes (PDB-IDs), are 1WDY, 3V31, 3V30, 3V2X, 3V2O, 3UXG, 3TWQ-3TWX, 1N11, 1S70 and 2ZGD.

Examples of designed ankyrin repeat protein libraries, such as the N2C and N3C designed ankyrin repeat protein libraries, are described (WO 2002/020565; Binz et al. 2003, loc. cit.; Binz et al. 2004, loc. cit.). The digit in N2C and N3C describes the number of randomized repeat modules present between the N-terminal and C-terminal capping modules.

The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of a ankyrin repeat module of the current disclosure and consequently position 33 of a ankyrin repeat module of Binz et al. 2004, loc. cit. corresponds to position 1 of a following ankyrin repeat module of the current disclosure.

All the DNA sequences were confirmed by sequencing, and the calculated molecular weight of all described proteins was confirmed by mass spectrometry.

Example 1

Selection of Binding Proteins Comprising an Ankyrin Repeat Domain with Binding Specificity for HGF Using ribosome display (Hanes, J. and Plückthun, A., PNAS 94, 4937-42, 1997) many designed ankyrin repeat proteins (DARPins) with binding specificity for HGF were selected from DARPin libraries as described by Binz et al. 2004 (loc. cit.). The binding of the selected clones toward specific (HGF) and unspecific (MBP, E. coli maltose binding protein) targets was assessed by crude extract ELISA, indicating that hundreds of HGF binding proteins were successfully selected. For example, the ankyrin repeat domains of SEQ ID NO: 33 to 61 constitute amino acid sequences of selected binding proteins comprising an ankyrin repeat domain with binding specificity for HGF. Individual ankyrin repeat modules from such ankyrin repeat domains with binding specificity to HGF are provided in SEQ ID NO: 12 to 25.

Selection of HGF Specific Ankyrin Repeat Proteins by Ribosome Display

The selection of HGF specific ankyrin repeat proteins was performed by ribosome display (Hanes and Plückthun, loc. cit.) using human and/or mouse HGF as target proteins, libraries of designed ankyrin repeat proteins as described above and established protocols (Zahnd, C., Amstutz, P. and Plückthun, A., Nat. Methods 4, 69-79, 2007). The number of reverse transcription (RT)-PCR cycles after each selection round was constantly reduced from 45 to 25, adjusting to the yield due to enrichment of binders. The first four rounds of selection employed standard ribosome display selection, using decreasing target concentration and increasing washing stringency to increase selection pressure from round 1 to round 4 (Binz et al. 2004, loc. cit.). To enrich high affinity anti-HGF DARPins, the output from the fourth round of standard ribosome display selection (above) was subjected to one or two off-rate selection rounds with increased selection stringency (Zahnd, 2007, loc. cit.). A final standard selection round was performed after each off-rate selection round to amplify and recover the off-rate selected binding proteins. To increase the incidence of selected binders cross-reactive to human and mouse HGF, an additional selection round was performed on mouse HGF after having done an off-rate selection round on human HGF.

Selected Clones Bind Specifically to HGF as Shown by Crude Extract Receptor Competition ELISA Individual selected DARPins specifically binding HGF were identified by a receptor competition enzyme-linked immunosorbent assay (ELISA) using crude Escherichia coli extracts of DARPin expression cells using standard protocols. DARPins selected by ribosome display were cloned into the pQE30 (Qiagen) expression vector, transformed into E. coli XL1-Blue (Stratagene) and then grown overnight at 37° C. in a 96-deep-well plate (each clone in a single well) containing 1.2 ml growth medium (TB containing 1% glucose and 50 µg/ml ampicillin). 0.9 ml of fresh LB medium containing 50 µg/ml ampicillin was inoculated with 50 µl of the overnight culture in a fresh 96-deep-well plate. After incubation for 60-90 minutes at 37° C., expression was induced with IPTG (0.5 mM final concentration) and continued for 3 to 4 hours. Cells were harvested, resuspended in 50 µl B-PERII (Pierce) and incubated for 15 min at room temperature with shaking. Then, 950 µl PBS was added and cell debris were removed by centrifugation. The extract of each lysed clone was applied as a 1:50 dilution in PBSTC (PBS supplemented with 0.1% Tween 20® and 0.25% (w/v) Casein, pH 7.4) together with 1 nM biotinylated human or mouse HGF, to a well of a Protein G coated MaxiSorp plate containing either human or mouse c-Met-Fc fusion and incubated for 10 minutes at RT. After extensive washing with PBS-T (PBS supplemented with 0.1% Tween 20®, pH 7.4) the plate was developed using standard ELISA procedures and streptavidin-HRP conjugate (11 089 153 001, Roche). Binding was then detected by POD substrate (Roche). The color development was measured at 405 nm. Screening of several hundred clones by such a crude cell extract ELISA revealed more than a hundred different DARPins with specificity for HGF. Examples of amino acid sequences of selected ankyrin repeat domains that specifically bind to human HGF are provided in SEQ ID NO:33 to 61.

These ankyrin repeat domains with binding specificity for HGF and negative control DARPins with no binding specificity for HGF (i.e. DARPin #28 and #29) were cloned into a pQE (QIAgen, Germany) based expression vector providing an N-terminal His-tag to facilitate simple protein purification as described below. For example, expression vectors encoding the following DARPins were constructed:

DARPin #33 (SEQ ID NO:33 with a His-tag (SEQ ID NO:9) fused to its N terminus);
DARPin #34 (SEQ ID NO:34 with a His-tag (SEQ ID NO:9) fused to its N terminus);
DARPin #35 (SEQ ID NO:35 with a His-tag (SEQ ID NO:9) fused to its N terminus);
DARPin #36 (SEQ ID NO:36 with a His-tag (SEQ ID NO:9) fused to its N terminus);
DARPin #37 (SEQ ID NO:37 with a His-tag (SEQ ID NO:9) fused to its N terminus);
DARPin #38 (SEQ ID NO:38 with a His-tag (SEQ ID NO:9) fused to its N terminus);
DARPin #39 (SEQ ID NO:39 with a His-tag (SEQ ID NO:9) fused to its N terminus);
DARPin #40 (SEQ ID NO:40 with a His-tag (SEQ ID NO:9) fused to its N terminus);
DARPin #41 (SEQ ID NO:41 with a His-tag (SEQ ID NO:9) fused to its N terminus);
DARPin #42 (SEQ ID NO:42 with a His-tag (SEQ ID NO:9) fused to its N terminus);
DARPin #43 (SEQ ID NO:43 with a His-tag (SEQ ID NO:9) fused to its N terminus);
DARPin #44 (SEQ ID NO:44 with a His-tag (SEQ ID NO:9) fused to its N terminus);
DARPin #45 (SEQ ID NO:45 with a His-tag (SEQ ID NO:9) fused to its N terminus);
DARPin #46 (SEQ ID NO:46 with a His-tag (SEQ ID NO:9) fused to its N terminus);
DARPin #47 (SEQ ID NO:47 with a His-tag (SEQ ID NO:9) fused to its N terminus);
DARPin #48 (SEQ ID NO:48 with a His-tag (SEQ ID NO:9) fused to its N terminus);
DARPin #49 (SEQ ID NO:49 with a His-tag (SEQ ID NO:9) fused to its N terminus);
DARPin #50 (SEQ ID NO:50 with a His-tag (SEQ ID NO:9) fused to its N terminus);
DARPin #51 (SEQ ID NO:51 with a His-tag (SEQ ID NO:9) fused to its N terminus);
DARPin #52 (SEQ ID NO:52 with a His-tag (SEQ ID NO:9) fused to its N terminus);
DARPin #53 (SEQ ID NO:53 with a His-tag (SEQ ID NO:9) fused to its N terminus);
DARPin #54 (SEQ ID NO:54 with a His-tag (SEQ ID NO:9) fused to its N terminus);
DARPin #55 (SEQ ID NO:55 with a His-tag (SEQ ID NO:9) fused to its N terminus);
DARPin #56 (SEQ ID NO:56 with a His-tag (SEQ ID NO:9) fused to its N terminus);
DARPin #57 (SEQ ID NO:57 with a His-tag (SEQ ID NO:9) fused to its N terminus);
DARPin #58 (SEQ ID NO:58 with a His-tag (SEQ ID NO:9) fused to its N terminus);
DARPin #59 (SEQ ID NO:59 with a His-tag (SEQ ID NO:9) fused to its N terminus);
DARPin #60 (SEQ ID NO:60 with a His-tag (SEQ ID NO:9) fused to its N terminus);
DARPin #61 (SEQ ID NO:61 with a His-tag (SEQ ID NO:9) fused to its N terminus); and
DARPin #62 (SEQ ID NO:62 with a Hi-tag (SEQ ID NO:9) fused to its N terminus;

High Level and Soluble Expression of DARPins

For further analysis, the selected clones showing specific HGF binding in the crude cell extract ELISA as described above were expressed in *E. coli* BL21 or XL1-Blue cells and purified using their His-tag using standard protocols. 25 ml of stationary overnight cultures (TB, 1% glucose, 100 mg/l of ampicillin; 37° C.) were used to inoculate 500 ml cultures (same medium). At an absorbance of 1.0 at 600 nm, the cultures were induced with 0.5 mM IPTG and incubated at 37° C. for 4-5 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Alternatively, DARPins or selected repeat domains devoid of a 6×His-tag were purified by anion exchange chromatography followed by size exclusion chromatography according to standard resins and protocols known to the person skilled in the art. Up to 200 mg of highly soluble DARPins with binding specificity to HGF can be purified from one liter of *E. coli* culture with a purity >95% as estimated from SDS-15% PAGE. Such purified DARPins are used for further characterizations.

Example 2

Characterization of the DARPins with Binding for Specificity for HGF by Surface Plasmon Resonance Analysis Human HGF molecules were directly immobilized in a flow cell and the interaction with various selected DARPins was analyzed.

Kd Determination by Surface Plasmon Resonance (SPR) Analysis

Figure 1:
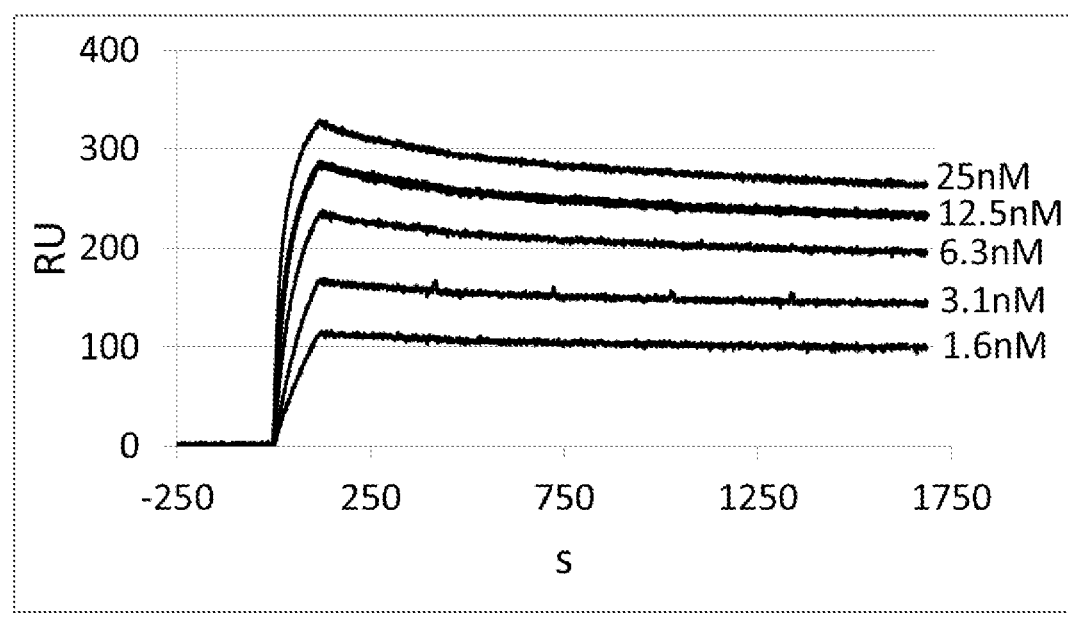
FIG. 1. Surface Plasmon Resonance analysis of a selected DARPin.

SPR was measured using a ProteOn instrument (BioRad) and measurement was performed according standard procedures known to the person skilled in the art. The running buffer was PBS, pH 7.4, containing 0.005% Tween 20®. Human HGF was covalently immobilized on a GLC chip (BioRad) to a level of about 5000 resonance units (RU). The interaction of DARPin and HGF was then measured by injecting 200 µl running buffer (PBS containing 0.005% Tween®) containing serial dilutions of DARPins of concentration of 25, 12.5, 6.26, 3.13 and 1.67 nM (on-rate measurement), followed by a running buffer flow for 25 minutes at a constant flow rate of 100 µl/min (off-rate measurement). The signals (i.e. resonance unit (RU) values) of the interspots and a reference injection (i.e. injection of running buffer only) were subtracted from the RU traces obtained after injection of DARPin (double-referencing). From the SPR traces obtained from the on-rate and off-rate measurements the on- and off-rate of the corresponding DARPin HGF interaction can be determined. As an example, FIG. 1 shows the obtained SPR traces for DARPin #51. Dissociation constants (Kd) were calculated from the estimated on- and off-rates using standard procedures known to the person skilled in the art. Kd values of selected DARPins were determined to be in the range of 10 pM to 20 nM. As an example, Table 1 summarizes the Kd values for some of the selected DARPins.

TABLE 1

Kd values of DARPin human HGF interactions

| DARPin # | Kd [pM] |
|---|---|
| DARPin #33 | 148 |
| DARPin #37 | 11 |
| DARPin #38 | 1600 |
| DARPin #42 | 84 |
| DARPin #43 | 25 |
| DARPin #48 | 16 |
| DARPin #51 | 51 |
| DARPin #56 | 736 |
| DARPin #57 | 16600 |
| DARPin #58 | 578 |
| DARPin #59 | 528 |
| DARPin #60 | 26 |
| DARPin #61 | 160 |

Competition SPR Analysis

To check if a binding protein of the invention competes for binding to HGF with an ankyrin repeat domain, competition SPR analysis was carried out by binding a first DARPin to saturation on human HGF and performing a subsequent injection of a second DARPin. When no increase in signal was seen upon injection of the second DARPin, the first and second DARPins were defined to compete for binding to HGF. When an increase in signal was seen, the first and second DARPins were defined to not compete for binding to HGF. An example analysis for each two DARPins competing for binding to HGF and two DARPins non-competing to HGF is given in FIG. 2.

Example 3

Inhibition of HGF Induced c-Met Phosphorylation by DARPins with Binding Specificity for HGF A549 cells were seeded in complete medium (DMEM; 10% FBS) in 96 well plates at 50,000 cells per well. 24 h later, medium was replaced by serum-free medium. Cells were incubated for another 24 h and stimulated by 1 nM human HGF in the presence and absence of DARPin. HGF and DARPin were preincubated for at least 30 min at room temperature prior to addition to cells. Cells were stimulated for 10 minutes under cell culture conditions. Stimulation was terminated by removing the cell supernatant (by flicking) and addition of cell lysis buffer (RIPA; Sample Diluent Concentrate 2; RnDSystems). Phosphorylated c-Met (P-cMet) levels in cell lysates were determined using the Human Phospho-HGF R/c-MET DuoSet IC (RnD Systems) according to the manufacturers' protocol. Data were analyzed using GraphPad Prism software (GraphPad Software Inc., CA, USA). The percentage inhibition of phosphorylation was calculated by setting the OD obtained in the non-stimulated control as 100% inhibition and the control without inhibitor as 0% inhibition. For the inhibition assay, the data were fitted to a log (inhibitor) versus response/variable slope.

Example results are summarized in Table 3. $IC_{50}$ values were calculated from the titration curves obtained as described above using standard procedures known to the person skilled in the art. % inhibition was calculated as described above. Example titration curves are given for DARPin #51 and DARPin #43 in FIG. 3.

TABLE 3

DARPin inhibition potency of HGF stimulated c-Met phosphorylation

| DARPin # | $IC_{50}$ [nM] | % inhibition |
|---|---|---|
| DARPin #33 | 0.20 | 100 |
| DARPin #37 | 0.07 | 95 |
| DARPin #38 | 2.59 | 88 |
| DARPin #41 | 0.13 | 99 |
| DARPin #42 | 0.32 | 98 |
| DARPin #43 | 0.16 | 101 |
| DARPin #48 | 0.10 | 95 |
| DARPin #51 | 0.01 | 81 |
| DARPin #56 | 0.53 | 72 |
| DARPin #57 | 1.72 | 100 |
| DARPin #58 | 1.63 | 89 |
| DARPin #59 | 0.85 | 100 |
| DARPin #60 | 0.05 | 94 |
| DARPin #61 | 0.39 | 82 |

Example 4

Inhibition of U87 Cell Proliferation by DARPins with Binding Specificity for HGF U87 cells were culture in DMEM containing 10% FBS (Promocell-cytokine-low) at 37° C. at 5% CO2. Cells were split in a 1:3 ratio twice a week. 2500 cells per 96 well were seeded in 100 ul DMEM containing 1% FBS and incubated overnight. The next day DARPins were added (10 ul of 10× final concentration) and incubated for another 5 days. At day 4 10 ul BrdU labeling solution was added (10 ul 1:1000 diluted) per well. On day 5 the assay was analyzed according to the manufacturer's protocol. DARPins were titrated in a range of 1,000 nM down to 2 nM. The experiment was analyzed using the GraphPad Prism software. IC50s were calculated from a non-linear fit of the obtained titration curves.

Example results are summarized in Table 4. $IC_{50}$ values were calculated from the titration curves obtained as described above using standard procedures known to the person skilled in the art. Example titration curves are given for DARPin #51 and DARPin #43 in FIG. 4.

TABLE 4

Inhibition of U87 proliferation by DARPins binding HGF

| DARPin # | $IC_{50}$ [nM] |
|---|---|
| 33 | 137 |
| 37 | 400 |
| 41 | 113 |
| 42 | 82 |
| 43 | 71 |
| 51 | 116 |
| 57 | 730 |
| 59 | 3'280 |
| 60 | 78 |

Example 5

Characterization of DARPins with Binding Specificity for HGF by Receptor Competition Assay The potency of anti-HGF DARPins to inhibit the binding of human HGF to its receptor c-Met was determined in a receptor competition ELISA. c-Met (Fc chimera; RnD systems, USA, 358-MT-100/CF) was pre-coated on a microplate. DARPins and HGF were premixed in PBSTC and incubated at room temperature for 0.5 hours. These preincubation mixtures were then transferred into the with c-Met precoated wells and any HGF that was not blocked by the DARPins was bound by the immobilized receptor. After washing away any unbound substances, an polyclonal antibody specific for HGF (RnD systems, USA, AF-294-NA) was added to the wells. After washing away any unbound substances, an horse radish peroxidase conjugated antibody (Novus Biologicals, USA, NB7357) binding to the polyclonal antibody specific for HGF was added to the wells. Following a wash to remove any unbound antibody-enzyme reagent, a substrate solution (Roche, Switzerland, 11484281001) was added to the wells and color was developing in proportion to the amount of HGF bound. The color development was stopped and the intensity of the color was measured at 405 nm. In this assay, the tested DARPins showed high HGF inhibition potency. Example results are summarized in Table 5. Example titration curves are given for a set of DARPins in FIG. 5. $IC_{50}$ values were calculated from such titration curves obtained as described above using standard procedures known to the person skilled in the art.

TABLE 5

Inhibition of the HGF interaction with its receptor c-Met by DARPins

| DARPin # | $IC_{50}$ [nM] |
| --- | --- |
| 37 | 1.33 |
| 43 | 1.36 |
| 48 | 0.91 |
| 51 | 0.62 |

TABLE 5-continued

Inhibition of the HGF interaction with its receptor c-Met by DARPins

| DARPin # | $IC_{50}$ [nM] |
| --- | --- |
| 57 | 1.71 |
| 60 | 0.95 |

Example 6

Inhibition of U87 Tumor Growth by DARPins with Binding Specificity for HGF $10^7$ U87-MG cells were subcutaneously injected into the right flank of Swiss nude mice. 25 days later, when tumors reached an average size of 126±51 mm3 mice were randomly distributed to the treatment groups with 8 mice per group and treatment was started. The mice received seven i.v injections of 0.1 ml of vehicle solution/PBS or various DARPins in PBS (at doses of 0.11 mg/kg, 1.1 mg/kg and 11 mg/kg) with a 3-day interval between each dosing (Q3Dx7). Body weight and tumor volume were monitored twice weekly. The experiment was terminated 21 days after treatment start. As an example, FIG. 6 shows the tumor volume plotted against the time of treatments given as days after treatment start with PEGylated DARPin #62. The DARPins used for this tumor growth inhibition experiment comprise a N-terminal His-tag (SEQ ID NO:9), an ankyrin repeat domain with binding specificity for HGF according the invention, a GS-linker (SEQ ID NO:10) and a C-terminal Cys residue. The protein moiety of the DARPins was purified by standard means using their His-tag and the coupled to a 40 kDa PEG using standard maleimide chemistry. Other well-known methods (other than PEGylation, see above) to prolong the terminal half-life of the ankyrin repeat domains of the invention could be used to test these domains on their in vivo efficacy in such a tumor model.

The invention claimed is:

1. A recombinant protein comprising an ankyrin repeat domain, wherein said ankyrin repeat domain binds HGF, and wherein said ankyrin repeat domain comprises an ankyrin repeat module having an amino acid sequence selected from the group consisting of (1) SEQ ID NO: 18 to 20, and (2) sequences in which up to 3 amino acids in SEQ ID NO: 18 to 20 are exchanged by another amino acid.

2. The recombinant protein of claim 1, wherein said ankyrin repeat module has an amino acid sequence selected from the group consisting of (1) SEQ ID NO: 19, and (2) sequences in which up to 3 amino acids in SEQ ID NO: 19 are exchanged by another amino acid.

3. A recombinant protein comprising an ankyrin repeat domain, wherein said ankyrin repeat domain binds to human HGF, and wherein said ankyrin repeat domain comprises an amino acid sequence with at least 92% amino acid sequence identity with any one of the ankyrin repeat domains of SEQ ID NOs: 37, 43, 48, 50 to 52, and 60, wherein G at position 1 and/or S at position 2 of said ankyrin repeat domains are optionally missing; and L at the second last position and/or N at the last position of said ankyrin repeat domains are optionally exchanged by A.

4. The recombinant protein of claim 3, wherein said ankyrin repeat domain comprises an amino acid sequence with at least 92% amino acid sequence identity with the ankyrin repeat domain of SEQ ID NO: 51, wherein G at position 1 and/or S at position 2 of said ankyrin repeat domain of SEQ ID NO: 51 are optionally missing; and L at the second last position and/or N at the last position of said ankyrin repeat domain of SEQ ID NO: 51 are optionally exchanged by A.

5. The recombinant protein of claim 3, wherein said ankyrin repeat domain is selected from the group consisting of the ankyrin repeat domains of SEQ ID NOs: 37, 43, 48, 50 to 52, and 60, wherein G at position 1 and/or S at position 2 of said ankyrin repeat domains are optionally missing; and L at the second last position and/or N at the last position of said ankyrin repeat domains are optionally exchanged by A.

6. The recombinant protein of claim 3, wherein said ankyrin repeat domain has the amino acid sequence of SEQ ID NO: 51, wherein G at position 1 and/or S at position 2 of SEQ ID NO: 51 are optionally missing; and L at the second last position and/or N at the last position of SEQ ID NO: 51 are optionally exchanged by A.

7. The recombinant protein of claim 1, comprising a peptide of any one of the sequences SEQ ID NO: 18 to 20, 37, 43, 48, 50 to 52, and 60.

8. A pharmaceutical composition comprising the recombinant protein of claim 1 and a pharmaceutically acceptable carrier and/or diluent.

9. A recombinant protein comprising an ankyrin repeat domain, wherein said ankyrin repeat domain binds human HGF, and wherein said ankyrin repeat domain comprises an ankyrin repeat module having an amino acid sequence selected from the group consisting of (SEQ ID NO: 18)
(1) KDRYGDTPLHLAADIGHLEIVEVLLKAGADVNA, wherein
K at position 1 is optionally exchanged by Q, H, I, V;
R at position 3 is optionally exchanged by A, T or N;
Y at position 4 is optionally exchanged by F or W;
D at position 6 is optionally exchanged by N;
D at position 14 is optionally exchanged by S;
I at position 15 is optionally exchanged by Y or A; and
E at position 19 is optionally exchanged by K;

(SEQ ID NO: 19)
(2) EDYFGNTPLHLAASYGHLEIVEVLLKAGADVNA, wherein
- E at position 1 is optionally exchanged by D, F, A, or L;
- Y at position 3 is optionally exchanged by W, S, or V;
- F at position 4 is optionally exchanged by Y;
- N at position 6 is optionally exchanged by D; and
- Y at position 15 is optionally exchanged by M, L, S, or A;

and (SEQ ID NO: 20)
(3) KDDYGNTPLHLAANTGHLEIVEVLLKAGADVNA, wherein
- K at position 1 is optionally exchanged by M, D, L, Q, or V;
- D at position 3 is optionally exchanged by Y, or T;
- Y at position 4 is optionally exchanged A, or N;
- T at position 15 is optionally exchanged by S;
- H at position 17 is optionally exchanged by R; and
- E at position 19 is optionally exchanged by K.

10. The recombinant protein of claim 3, wherein said ankyrin repeat domain binds human HGF in PBS with a dissociation constant ($K_D$) below $10^{-7}$M, wherein said ankyrin repeat domain comprises the amino acid sequence of any one of the ankyrin repeat domains of SEQ ID NOs: 37, 43, 48, 51 or 60, wherein G at position 1 and/or S at position 2 of said ankyrin repeat domains are optionally missing; and L at the second to last position and/or N at the last position of said ankyrin repeat domains are optionally exchanged by A.

11. The recombinant protein of claim 2, wherein said ankyrin repeat domain competes for binding to HGF with the ankyrin repeat domain of SEQ ID NO: 51.

12. A pharmaceutical composition comprising the recombinant protein of claim 4 and a pharmaceutically acceptable carrier and/or diluent.

13. A pharmaceutical composition comprising the recombinant protein of claim 9 and a pharmaceutically acceptable carrier and/or diluent.

14. The recombinant protein of claim 9, wherein said ankyrin repeat module has the amino acid sequence (SEQ ID NO: 19)
EDYFGNTPLHLAASYGHLEIVEVLLKAGADVNA, wherein
- E at position 1 is optionally exchanged by D, F, A, or L;
- Y at position 3 is optionally exchanged by W, S, or V;
- F at position 4 is optionally exchanged by Y;
- N at position 6 is optionally exchanged by D; and
- Y at position 15 is optionally exchanged by M, L, S, or A.

15. The recombinant protein of claim 14, wherein said ankyrin repeat domain further comprises an ankyrin repeat module having the amino acid sequence (SEQ ID NO: 20)
KDDYGNTPLHLAANTGHLEIVEVLLKAGADVNA, wherein
- K at position 1 is optionally exchanged by M, D, L, Q, or V;
- D at position 3 is optionally exchanged by Y, or T;
- Y at position 4 is optionally exchanged A, or N;
- T at position 15 is optionally exchanged by S;
- H at position 17 is optionally exchanged by R; and
- E at position 19 is optionally exchanged by K.

16. The recombinant protein of claim 15, wherein said ankyrin repeat domain further comprises an ankyrin repeat module having the amino acid sequence (SEQ ID NO: 18)
KDRYGDTPLHLAADIGHLEIVEVLLKAGADVNA, wherein
- K at position 1 is optionally exchanged by Q, H, I, V;
- R at position 3 is optionally exchanged by A, T or N;
- Y at position 4 is optionally exchanged by F or W;
- D at position 6 is optionally exchanged by N;
- D at position 14 is optionally exchanged by S;
- I at position 15 is optionally exchanged by Y or A; and
- E at position 19 is optionally exchanged by K.

17. The recombinant protein of claim 3, wherein said ankyrin repeat domain comprises an amino acid sequence with at least 95% amino acid sequence identity with the ankyrin repeat domain of SEQ ID NO: 51, wherein G at position 1 and/or S at position 2 of said ankyrin repeat domain of SEQ ID NO: 51 are optionally missing; and L at the second last position and/or N at the last position of said ankyrin repeat domain of SEQ ID NO: 51 are optionally exchanged by A.

18. The recombinant protein of claim 3, wherein said ankyrin repeat domain comprises an amino acid sequence with at least 98% amino acid sequence identity with the ankyrin repeat domain of SEQ ID NO: 51, wherein G at position 1 and/or S at position 2 of said ankyrin repeat domain of SEQ ID NO: 51 are optionally missing; and L at the second last position and/or N at the last position of said ankyrin repeat domain of SEQ ID NO: 51 are optionally exchanged by A.

19. The recombinant protein of claim 1, wherein said ankyrin repeat module has an amino acid sequence selected from the group consisting of (1) SEQ ID NO: 18 to 20, and (2) sequences in which up to 2 amino acids in SEQ ID NO: 18 to 20 are exchanged by another amino acid.

20. The recombinant protein of claim 1, wherein said ankyrin repeat module has an amino acid sequence selected from the group consisting of (1) SEQ ID NO: 18 to 20, and (2) sequences in which up to one amino acid in SEQ ID NO: 18 to 20 is exchanged by another amino acid.

21. The recombinant protein of claim 1, wherein said ankyrin repeat module has an amino acid sequence selected from the group consisting of SEQ ID NO: 18 to 20.

22. The recombinant protein of claim 1, wherein said ankyrin repeat module has the amino acid sequence of SEQ ID NO: 18, wherein said ankyrin repeat domain further comprises an ankyrin repeat module having the amino acid sequence of SEQ ID NO: 19 and an ankyrin repeat module having the amino acid sequence of SEQ ID NO: 20, and wherein in said ankyrin repeat domain said ankyrin repeat module having the amino acid sequence of SEQ ID NO: 19 follows said ankyrin repeat module having the amino acid sequence of SEQ ID NO: 18 and said ankyrin repeat module having the amino acid sequence of SEQ ID NO: 20 follows said ankyrin repeat module having the amino acid sequence of SEQ ID NO: 19.

* * * * *

UNITED STATES PATENT AND TRADEMARK OFFICE
CERTIFICATE OF CORRECTION

| | |
|---|---|
| PATENT NO. | : 11,453,708 B2 |
| APPLICATION NO. | : 14/891792 |
| DATED | : September 27, 2022 |
| INVENTOR(S) | : Gaby Tresch et al. |

It is certified that error appears in the above-identified patent and that said Letters Patent is hereby corrected as shown below:

On the Title Page

Item (72), Line 2, under "Inventors," "Talitha Bakker, Birmensdorf (CH);" should read --Talitha Rianne Bakker, Birmensdorf (CH);--.

Item (72), Lines 4-5, "Kasper H. Binz, Birmensdorf (CH)" should read --H. Kaspar Binz, Birmensdorf (CH)--.

Item (30), under "Foreign Application Priority Data," "13170056" should read --13170056.9--.

Signed and Sealed this
Twentieth Day of December, 2022

Katherine Kelly Vidal
*Director of the United States Patent and Trademark Office*

SEQUENCE LISTING

```
<160> NUMBER OF SEQ ID NOS: 65

<210> SEQ ID NO 1
<211> LENGTH: 32
<212> TYPE: PRT
<213> ORGANISM: Artificial Sequence
<220> FEATURE:
<223> OTHER INFORMATION: Capping module

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Capping module

<400> SEQUENCE: 2

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30
```

<210> SEQ ID NO 3
<211> LENGTH: 32
<212> TYPE: PRT
<213> ORGANISM: Artificial Sequence
<220> FEATURE:
<223> OTHER INFORMATION: capping module

<400> SEQUENCE: 3

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: capping module

<400> SEQUENCE: 4

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: capping module

<400> SEQUENCE: 5

Gln Asp Lys Phe Gly Lys Thr Pro Phe Asp Leu Ala Ile Arg Glu Gly
1               5                   10                  15

His Glu Asp Ile Ala Glu Val Leu Gln Lys Ala Ala
            20                  25

<210> SEQ ID NO 6
<211> LENGTH: 28
<212> TYPE: PRT
<213> ORGANISM: Artificial Sequence
<220> FEATURE:
<223> OTHER INFORMATION: capping module

<400> SEQUENCE: 6

Gln Asp Lys Phe Gly Lys Thr Pro Phe Asp Leu Ala Ile Asp Asn Gly
1               5                   10                  15

Asn Glu Asp Ile Ala Glu Val Leu Gln Lys Ala Ala
            20                  25

<210> SEQ ID NO 7
<211> LENGTH: 28
<212> TYPE: PRT
<213> ORGANISM: Artificial Sequence
<220> FEATURE:
<223> OTHER INFORMATION: capping module

<400> SEQUENCE: 7

Gln Asp Lys Phe Gly Lys Thr Pro Ala Asp Ile Ala Ala Asp Asn Gly
1               5                   10                  15

His Glu Asp Ile Ala Glu Val Leu Gln Lys Leu Asn 20                  25

<210> SEQ ID NO 8
<211> LENGTH: 28
<212> TYPE: PRT
<213> ORGANISM: Artificial Sequence
<220> FEATURE:
<223> OTHER INFORMATION: capping module

<400> SEQUENCE: 8

Gln Asp Lys Phe Gly Lys Thr Pro Ala Asp Ile Ala Ala Asp Asn Gly
1               5                   10                  15

His Glu Asp Ile Ala Glu Val Leu Gln Lys Leu Asn
            20                  25

<210> SEQ ID NO 9
<211> LENGTH: 10
<212> TYPE: PRT
<213> ORGANISM: Artificial Sequence
<220> FEATURE:
<223> OTHER INFORMATION: His-tag

<400> SEQUENCE: 9

Met Arg Gly Ser His His His His His His
1               5                   10

<210> SEQ ID NO 10
<211> LENGTH: 20
<212> TYPE: PRT
<213> ORGANISM: Artificial Sequence
<220> FEATURE:
<223> OTHER INFORMATION: GS-linker

<400> SEQUENCE: 10

Gly Gly Gly Gly Ser Gly Gly Gly Ser Gly Gly Gly Ser Gly
1               5                   10                  15

Gly Gly Gly Ser
            20

<210> SEQ ID NO 11
<211> LENGTH: 20
<212> TYPE: PRT
<213> ORGANISM: Artificial Sequence
<220> FEATURE:
<223> OTHER INFORMATION: PT-linker

<400> SEQUENCE: 11

Pro Thr Pro Thr Pro Thr Thr Pro Thr Pro Thr Pro Thr Thr Pro Thr
1               5                   10                  15

Pro Thr Pro Thr
            20

<210> SEQ ID NO 12
<211> LENGTH: 33
<212> TYPE: PRT
<213> ORGANISM: Artificial Sequence
<220> FEATURE:
<223> OTHER INFORMATION: AR module (M 1.0)

<400> SEQUENCE: 12

His Asp Tyr Ser Gly Phe Thr Pro Leu His Leu Ala Ala Tyr Tyr Gly
1               5                   10                  15

His Leu Glu Ile Val Glu Val Leu Leu Lys His Gly Ala Asp Val Asn
            20                  25                  30

Ala

<210> SEQ ID NO 13
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 13

Phe Asp Asp Trp Gly His Thr Pro Leu His Leu Ala Ala Arg Tyr Gly
1               5                   10                  15

His Leu Glu Ile Val Glu Val Leu Leu Lys Tyr Gly Ala Asp Val Asn
            20                  25                  30

Ala

<210> SEQ ID NO 14
<211> LENGTH: 33
<212> TYPE: PRT
<213> ORGANISM: Artificial Sequence
<220> FEATURE:
<223> OTHER INFORMATION: AR module (M 1.0)

<400> SEQUENCE: 14

Glu Asp Thr Glu Gly Tyr Thr Pro Leu His Leu Ala Ala Met Asp Gly
1               5                   10                  15

His Leu Glu Ile Val Glu Val Leu Leu Lys Asn Gly Ala Asp Val Asn
            20                  25                  30

Ala

<210> SEQ ID NO 15
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 15

Lys Tyr Glu Asp Gly Leu Thr Pro Leu His Leu Ala Ala Phe Tyr Gly
1               5                   10                  15

His Leu Glu Ile Val Glu Val Leu Leu Arg His Gly Ala Asp Val Asn
            20                  25                  30

Ala

<210> SEQ ID NO 16
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 16

Thr Asp Ala Trp Gly His Thr Pro Leu His Leu Ala Ala Tyr Leu Gly
1               5                   10                  15

His Leu Glu Ile Val Glu Val Leu Leu Lys Tyr Gly Ala Asp Val Asn
            20                  25                  30

Ala

<210> SEQ ID NO 17
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 17

Glu Asp Thr Glu Gly Tyr Thr Pro Leu His Leu Ala Ala Met Asp Gly
1               5                   10                  15

His Leu Glu Ile Ile Glu Val Leu Leu Lys His Gly Ala Asp Val Asn
            20                  25                  30

Ala

<210> SEQ ID NO 18
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 18

Lys Asp Arg Tyr Gly Asp Thr Pro Leu His Leu Ala Ala Asp Ile Gly
1               5                   10                  15

His Leu Glu Ile Val Glu Val Leu Leu Lys Ala Gly Ala Asp Val Asn
            20                  25                  30

Ala

<210> SEQ ID NO 19
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 19

Glu Asp Tyr Phe Gly Asn Thr Pro Leu His Leu Ala Ala Ser Tyr Gly
1               5                   10                  15

His Leu Glu Ile Val Glu Val Leu Leu Lys Ala Gly Ala Asp Val Asn
            20                  25                  30

Ala

<210> SEQ ID NO 20
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 20

Lys Asp Asp Tyr Gly Asn Thr Pro Leu His Leu Ala Ala Asn Thr Gly
1               5                   10                  15

His Leu Glu Ile Val Glu Val Leu Leu Lys Ala Gly Ala Asp Val Asn
            20                  25                  30

Ala

<210> SEQ ID NO 21
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 21

His Asp Thr Trp Gly Leu Thr Pro Leu His Leu Ala Ala Phe His Gly
1               5                   10                  15

His Gln Glu Ile Val Glu Val Leu Leu Lys His Gly Ala Asp Val Asn
            20                  25                  30

Ala

<210> SEQ ID NO 22
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 22

Gln Asp Phe Tyr Gly Lys Thr Pro Leu His Leu Ala Ala Leu Arg Gly
1               5                   10                  15

His Leu Glu Ile Val Glu Val Leu Leu Lys Tyr Gly Ala Asp Val Asn
            20                  25                  30

Ala

<210> SEQ ID NO 23
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 23

His Asp Tyr Leu Gly Leu Thr Pro Leu His Leu Ala Ala Ser Asp Gly
1               5                   10                  15

His Leu Glu Ile Val Glu Val Leu Leu Lys His Gly Ala Asp Val Asn
            20                  25                  30

Ala

<210> SEQ ID NO 24
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 24

Tyr Asp Tyr Asn Gly Leu Thr Pro Leu His Leu Ala Ala Asn Asn Gly
1               5                   10                  15

His Leu Glu Ile Val Glu Val Leu Leu Lys Tyr Gly Ala Asp Val Asn
            20                  25                  30

Ala

<210> SEQ ID NO 25
<211> LENGTH: 33
<212> TYPE: PRT
<213> ORGANISM: Artificial Sequence
<220> FEATURE:
<223> OTHER INFORMATION: AR module (M1.0)

<400> SEQUENCE: 25

Phe Asp Val Ala Gly Tyr Thr Pro Leu His Leu Ala Ala Tyr Phe Gly
1               5                   10                  15

His Leu Glu Ile Val Glu Val Leu Leu Lys Tyr Gly Ala Asp Val Asn
            20                  25                  30

Ala

```
<210> SEQ ID NO 26
<211> LENGTH: 33
<212> TYPE: PRT
<213> ORGANISM: Artificial Sequence
<220> FEATURE:
<223> OTHER INFORMATION: AR sequence motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 26

Xaa Asp Xaa Xaa Gly Xaa Thr Pro Leu His Leu Ala Ala Xaa Xaa Gly
 1               5                  10                  15

His Leu Glu Ile Val Glu Val Leu Leu Lys Xaa Gly Ala Asp Val Asn
            20                  25                  30

Ala

<210> SEQ ID NO 27
<211> LENGTH: 33
<212> TYPE: PRT
<213> ORGANISM: Artificial Sequence
<220> FEATURE:
<223> OTHER INFORMATION: AR sequence motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 27

Lys Asp Xaa Xaa Gly Xaa Thr Pro Leu His Leu Ala Ala Xaa Xaa Gly
 1               5                  10                  15

His Leu Glu Ile Val Glu Val Leu Leu Lys Ala Gly Ala Asp Val Asn
            20                  25                  30

Ala

<210> SEQ ID NO 28
<211> LENGTH: 33
<212> TYPE: PRT
<213> ORGANISM: Artificial Sequence
<220> FEATURE:
<223> OTHER INFORMATION: AR sequence motif
<220> FEATURE:
<221> NAME/KEY: misc_feature
<222> LOCATION: (3)..(4)
<223> OTHER INFORMATION: Xaa can be any naturally occurring amino acid
<220> FEATURE:
```

```
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 28

Lys Asp Xaa Xaa Gly Xaa Thr Pro Leu His Xaa Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 29
<211> LENGTH: 32
<212> TYPE: PRT
<213> ORGANISM: Artificial Sequence
<220> FEATURE:
<223> OTHER INFORMATION: AR sequence motif
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 29

Gly Ser Asp Leu Gly Xaa Lys Leu Leu Xaa Ala Ala Xaa Xaa Gly Gln
1               5                   10                  15

Asp Asp Glu Val Arg Ile Leu Leu Ala Ala Gly Ala Asp Val Asn Ala
            20                  25                  30

<210> SEQ ID NO 30
<211> LENGTH: 28
<212> TYPE: PRT
<213> ORGANISM: Artificial Sequence
<220> FEATURE:
<223> OTHER INFORMATION: AR sequence motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 30

Gln Asp Xaa Xaa Gly Xaa Thr Pro Ala Asp Leu Ala Ala Xaa Xaa Gly
1               5                   10                  15

His Glu Asp Ile Ala Glu Val Leu Gln Lys Leu Asn
            20                  25
```

-continued

```
<210> SEQ ID NO 31
<211> LENGTH: 159
<212> TYPE: PRT
<213> ORGANISM: Artificial Sequence
<220> FEATURE:
<223> OTHER INFORMATION: AR domain

<400> SEQUENCE: 31

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Asn Asp Gly Tyr Thr Pro Leu His Leu Ala Ala Ser Asn Gly
        35                  40                  45

His Leu Glu Ile Val Glu Val Leu Leu Lys Asn Gly Ala Asp Val Asn
    50                  55                  60

Ala Ser Asp Leu Thr Gly Ile Thr Pro Leu His Leu Ala Ala Ala Thr
65                  70                  75                  80

Gly His Leu Glu Ile Val Glu Val Leu Leu Lys His Gly Ala Asp Val
                85                  90                  95

Asn Ala Tyr Asp Asn Asp Gly His Thr Pro Leu His Leu Ala Ala Lys
            100                 105                 110

Tyr Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 32
<211> LENGTH: 126
<212> TYPE: PRT
<213> ORGANISM: Artificial Sequence
<220> FEATURE:
<223> OTHER INFORMATION: AR domain

<400> SEQUENCE: 32

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Lys Asp Gly Tyr Thr Pro Leu His Leu Ala Ala Arg Glu Gly
        35                  40                  45

His Leu Glu Ile Val Glu Val Leu Leu Lys Ala Gly Ala Asp Val Asn
    50                  55                  60

Ala Lys Asp Lys Asp Gly Tyr Thr Pro Leu His Leu Ala Ala Arg Glu
65                  70                  75                  80

Gly His Leu Glu Ile Val Glu Val Leu Leu Lys Ala Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 33
<211> LENGTH: 159
<212> TYPE: PRT
<213> ORGANISM: Artificial Sequence
<220> FEATURE:
```

<223> OTHER INFORMATION: AR domain

<400> SEQUENCE: 33

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Tyr Ser Gly Phe Thr Pro Leu His Leu Ala Ala Tyr Tyr Gly
        35                  40                  45

His Leu Glu Ile Val Glu Val Leu Leu Lys His Gly Ala Asp Val Asn
    50                  55                  60

Ala Phe Asp Asp Trp Gly His Thr Pro Leu His Leu Ala Ala Arg Tyr
65                  70                  75                  80

Gly His Leu Glu Ile Val Glu Val Leu Leu Lys Tyr Gly Ala Asp Val
            85                  90                  95

Asn Ala Glu Asp Thr Glu Gly Tyr Thr Pro Leu His Leu Ala Ala Met
            100                 105                 110

Asp Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 34
<211> LENGTH: 159
<212> TYPE: PRT
<213> ORGANISM: Artificial Sequence
<220> FEATURE:
<223> OTHER INFORMATION: AR domain

<400> SEQUENCE: 34

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ile Asp Tyr Ser Gly Phe Thr Pro Leu His Leu Ala Ala Tyr Tyr Gly
        35                  40                  45

His Leu Glu Ile Val Glu Val Leu Leu Lys His Gly Ala Asp Val Asn
    50                  55                  60

Ala Phe Asp Asp Trp Gly His Thr Pro Leu His Leu Ala Ala Arg Tyr
65                  70                  75                  80

Gly His Leu Glu Ile Val Glu Val Leu Leu Lys Tyr Gly Ala Asp Val
            85                  90                  95

Asn Ala Glu Asp Thr Glu Gly Tyr Thr Pro Leu His Leu Ala Ala Met
            100                 105                 110

Asp Gly His Leu Glu Ile Val Glu Val Leu Leu Lys Tyr Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 35
<211> LENGTH: 159
<212> TYPE: PRT
<213> ORGANISM: Artificial Sequence
<220> FEATURE:
<223> OTHER INFORMATION: AR domain

<400> SEQUENCE: 35

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Met Ser Gly Phe Thr Pro Leu His Leu Ala Ala Phe Tyr Gly
        35                  40                  45

His Leu Glu Ile Val Glu Val Leu Leu Lys His Gly Ala Asp Val Asn
    50                  55                  60

Ala Glu Asp Tyr Trp Gly His Thr Pro Leu His Leu Ala Ala Arg Tyr
65                  70                  75                  80

Gly His Leu Glu Ile Val Glu Val Leu Leu Lys Tyr Gly Ala Asp Val
                85                  90                  95

Asn Ala Glu Asp Thr Glu Gly Tyr Thr Pro Leu His Leu Ala Ala Met
            100                 105                 110

Asp Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 36
<211> LENGTH: 126
<212> TYPE: PRT
<213> ORGANISM: Artificial Sequence
<220> FEATURE:
<223> OTHER INFORMATION: AR domain

<400> SEQUENCE: 36

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asn Asp Asp Ser Gly Phe Thr Pro Leu His Leu Ala Ala Phe Tyr Gly
        35                  40                  45

His Leu Glu Leu Val Glu Val Leu Leu Lys Tyr Gly Ala Asp Val Asn
    50                  55                  60

Ala Thr Asp Arg Phe Gly Leu Thr Pro Leu His Leu Ala Ala His Tyr
65                  70                  75                  80

Gly His Leu Glu Ile Val Glu Val Leu Leu Lys His Gly Asp Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 37
<211> LENGTH: 159
<212> TYPE: PRT
<213> ORGANISM: Artificial Sequence
<220> FEATURE:
<223> OTHER INFORMATION: AR domain

<400> SEQUENCE: 37

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Leu Thr Gly Phe Thr Pro Leu His Leu Ala Ala Tyr Tyr Gly
        35                  40                  45

His Leu Glu Ile Val Glu Val Leu Leu Lys Tyr Gly Ala Asp Val Asn
    50                  55                  60

Ala Asp Asp Arg Tyr Gly Leu Thr Pro Leu His Leu Ala Ala Asn Thr
65                  70                  75                  80

Gly His Leu Glu Ile Val Glu Val Leu Leu Lys Asn Gly Ala Asp Val
            85                  90                  95

Asn Ala Ser Asp Ser Val Gly Thr Thr Leu Leu His Leu Ala Ala Tyr
            100                 105                 110

Ile Gly His Pro Glu Ile Val Glu Val Leu Leu Lys Tyr Gly Ala Asp
            115                 120                 125

Val Asn Ala Gln Asp Lys Phe Gly Lys Thr Ala Phe Asp Ile Ser Ile
            130                 135                 140

Asp Asn Gly Asn Glu Asp Leu Ala Glu Ile Leu Gln Lys Leu Asn
145                 150                 155
```

<210> SEQ ID NO 38
<211> LENGTH: 126
<212> TYPE: PRT
<213> ORGANISM: Artificial Sequence
<220> FEATURE:
<223> OTHER INFORMATION: AR domain

<400> SEQUENCE: 38

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Ala Asn Gly Phe Thr Pro Leu His Leu Ala Ala Phe Tyr Gly
        35                  40                  45

His Leu Glu Ile Val Glu Val Leu Leu Lys Tyr Gly Ala Asp Val Asn
    50                  55                  60

Ala Tyr Asp Asn Phe Gly Leu Thr Pro Leu His Leu Ala Ala Ser Tyr
65                  70                  75                  80

Gly His Leu Glu Ile Val Glu Val Leu Leu Lys Asn Gly Ala Asp Val
            85                  90                  95

Tyr Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
            115                 120                 125
```

<210> SEQ ID NO 39
<211> LENGTH: 159
<212> TYPE: PRT
<213> ORGANISM: Artificial Sequence
<220> FEATURE:
<223> OTHER INFORMATION: AR domain

<400> SEQUENCE: 39

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30
```

Lys Tyr Glu Asp Gly Leu Thr Pro Leu His Leu Ala Ala Phe Tyr Gly
            35                  40                  45

His Leu Glu Ile Val Glu Val Leu Leu Lys His Gly Ala Asp Val Asn
     50                  55                  60

Ala Thr Asp Ala Trp Gly His Thr Pro Leu His Leu Ala Ala Ser Asn
65                  70                  75                  80

Gly His Leu Glu Ile Val Glu Val Leu Leu Lys Tyr Gly Ala Asp Val
                85                  90                  95

Asn Ala Ser Asp Thr Ala Gly Ile Thr Pro Leu His Leu Ala Ala His
            100                 105                 110

Asn Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 40
<211> LENGTH: 159
<212> TYPE: PRT
<213> ORGANISM: Artificial Sequence
<220> FEATURE:
<223> OTHER INFORMATION: AR domain

<400> SEQUENCE: 40

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Tyr Glu Asp Gly Leu Thr Pro Leu His Leu Ala Ala Phe Tyr Gly
            35                  40                  45

His Leu Glu Ile Val Glu Val Leu Leu Lys His Gly Ala Asp Val Asn
     50                  55                  60

Ala Thr Asp Ala Trp Gly His Thr Pro Leu His Leu Ala Ala Ala Tyr
65                  70                  75                  80

Gly His Leu Glu Ile Val Glu Val Leu Leu Lys Asn Gly Ala Asp Val
                85                  90                  95

Asn Ala His Asp Asn Val Gly Asp Thr Pro Leu His Leu Ala Ala Met
            100                 105                 110

Leu Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 41
<211> LENGTH: 159
<212> TYPE: PRT
<213> ORGANISM: Artificial Sequence
<220> FEATURE:
<223> OTHER INFORMATION: AR domain

<400> SEQUENCE: 41

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

```
            20                  25                  30
Lys Tyr Glu Asp Gly Leu Thr Pro Leu His Leu Ala Ala Phe Tyr Gly
        35                  40                  45

His Leu Glu Ile Val Glu Val Leu Leu Arg His Gly Ala Asp Val Asn
    50                  55                  60

Ala Thr Asp Ala Trp Gly His Thr Pro Leu His Leu Ala Ala Tyr Leu
65                  70                  75                  80

Gly His Leu Glu Ile Val Glu Val Leu Leu Lys Tyr Gly Ala Asp Val
                85                  90                  95

Asn Ala Glu Asp Thr Glu Gly Tyr Thr Pro Leu His Leu Ala Ala Met
            100                 105                 110

Asp Gly His Leu Glu Ile Ile Glu Val Leu Leu Lys His Gly Ala Asp
                115                 120                 125

Val Asn Ala Gln Asp Lys Phe Gly Lys Thr Ala Phe Asp Ile Ser Ile
            130                 135                 140

Asp Asn Gly Asn Glu Asp Leu Ala Glu Ile Leu Gln Lys Leu Asn
145                 150                 155

<210> SEQ ID NO 42
<211> LENGTH: 159
<212> TYPE: PRT
<213> ORGANISM: Artificial Sequence
<220> FEATURE:
<223> OTHER INFORMATION: AR domain

<400> SEQUENCE: 42

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Tyr Glu Asp Gly Leu Thr Pro Leu His Leu Ala Ala Phe Tyr Gly
        35                  40                  45

His Leu Glu Ile Val Glu Val Leu Leu Lys His Gly Ala Asp Val Asn
    50                  55                  60

Ala Thr Asp Ala Trp Gly His Thr Pro Leu His Leu Ala Ala His Tyr
65                  70                  75                  80

Gly His Leu Glu Ile Val Glu Val Leu Leu Lys Tyr Gly Ala Asp Val
                85                  90                  95

Asn Ala Ile Asp Thr Leu Gly Tyr Thr Pro Leu His Leu Ala Ala Asn
            100                 105                 110

Phe Gly His Leu Glu Ile Val Glu Val Leu Leu Lys Asn Gly Ala Asp
                115                 120                 125

Val Asn Ala Gln Asp Lys Phe Gly Lys Thr Ala Phe Asp Ile Ser Ile
            130                 135                 140

Asp Asn Gly Asn Glu Asp Leu Ala Glu Ile Leu Gln Lys Leu Asn
145                 150                 155

<210> SEQ ID NO 43
<211> LENGTH: 159
<212> TYPE: PRT
<213> ORGANISM: Artificial Sequence
<220> FEATURE:
<223> OTHER INFORMATION: AR domain

<400> SEQUENCE: 43

Gly Ser Asp Leu Gly Lys Lys Leu Leu Glu Ala Ala Arg Ala Gly Gln
1               5                   10                  15
```

```
Asp Asp Glu Val Arg Ile Leu Met Ala Asn Gly Ala Asp Val Asn Ala
            20                  25                  30

Lys Tyr Glu Asp Gly Leu Thr Pro Leu His Leu Ala Ala Phe Tyr Gly
        35                  40                  45

His Leu Glu Ile Val Glu Val Leu Leu Lys His Gly Ala Asp Val Asn
    50                  55                  60

Ala Thr Asp Ala Trp Gly His Thr Pro Leu His Leu Ala Ala Tyr Tyr
65                  70                  75                  80

Gly His Leu Glu Ile Val Glu Val Leu Leu Lys Tyr Gly Ala Asp Val
                85                  90                  95

Asn Thr His Asp Lys Glu Gly Met Thr Ala Leu His Leu Ala Ala Leu
            100                 105                 110

Thr Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 44
<211> LENGTH: 159
<212> TYPE: PRT
<213> ORGANISM: Artificial Sequence
<220> FEATURE:
<223> OTHER INFORMATION: AR domain

<400> SEQUENCE: 44

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

His Asp Asn Phe Gly Asp Thr Pro Leu His Leu Ala Ala Ser Ile Gly
        35                  40                  45

His Leu Glu Ile Val Glu Val Leu Leu Lys His Gly Ala Asp Val Asn
    50                  55                  60

Ala Phe Asp Ser Tyr Gly Asp Thr Pro Leu His Leu Ala Ala Ser Ser
65                  70                  75                  80

Gly His Leu Glu Ile Val Glu Val Leu Leu Lys Tyr Gly Ala Asp Val
                85                  90                  95

Asn Ala Leu Asp Tyr Asn Gly Asn Thr Pro Leu His Leu Ala Ala Asn
            100                 105                 110

Ser Gly Arg Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 45
<211> LENGTH: 159
<212> TYPE: PRT
<213> ORGANISM: Artificial Sequence
<220> FEATURE:
<223> OTHER INFORMATION: AR domain

<400> SEQUENCE: 45

Gly Ser Asp Leu Gly Lys Lys Leu Leu Glu Ala Ala Arg Ala Gly Gln
1               5                   10                  15
```

```
Asp Asp Glu Val Arg Ile Leu Met Ala Asn Gly Ala Asp Val Asn Ala
            20                  25                  30

Val Asp Ala Trp Gly Asp Thr Pro Leu His Leu Ala Ala Ser Ile Gly
        35                  40                  45

His Leu Glu Ile Val Glu Val Leu Leu Lys Asn Gly Ala Asp Val Asn
 50                  55                  60

Ala Ala Asp Tyr Tyr Gly Asp Thr Pro Leu His Leu Ala Ala Ser Ala
 65                  70                  75                  80

Gly His Leu Glu Ile Val Glu Val Leu Leu Lys Tyr Gly Ala Asp Val
                85                  90                  95

Asn Ala Gln Asp Asp Asn Gly Asn Thr Pro Leu His Leu Ala Ala Asn
            100                 105                 110

Thr Gly Arg Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

<210> SEQ ID NO 46
<211> LENGTH: 159
<212> TYPE: PRT
<213> ORGANISM: Artificial Sequence
<220> FEATURE:
<223> OTHER INFORMATION: AR domain

<400> SEQUENCE: 46

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
            20                  25                  30

Ile Asp Thr Trp Gly Asn Thr Pro Leu His Leu Ala Ala Asp Tyr Gly
        35                  40                  45

His Leu Glu Ile Val Glu Val Leu Leu Lys Asn Gly Ala Asp Val Asn
 50                  55                  60

Ala Leu Asp Trp Phe Gly Asp Thr Pro Leu His Leu Ala Ala Ser Leu
 65                  70                  75                  80

Gly His Leu Glu Ile Val Glu Val Leu Leu Lys Asn Gly Ala Asp Val
                85                  90                  95

Asn Ala Val Asp Thr Tyr Gly Asn Thr Pro Leu His Leu Ala Ala Asn
            100                 105                 110

Thr Gly Arg Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

<210> SEQ ID NO 47
<211> LENGTH: 159
<212> TYPE: PRT
<213> ORGANISM: Artificial Sequence
<220> FEATURE:
<223> OTHER INFORMATION: AR domain

<400> SEQUENCE: 47

Gly Ser Asp Leu Gly Lys Lys Leu Leu Glu Ala Ala Arg Ala Gly Gln

```
                1               5                  10                 15
Asp Asp Glu Val Arg Ile Leu Met Ala Asn Gly Ala Asp Val Asn Ala
                20                 25                 30

Gln Asp Arg Trp Gly Asp Thr Pro Leu His Leu Ala Ala Ser Ala Gly
            35                 40                 45

His Leu Lys Ile Val Glu Val Leu Leu Lys Tyr Gly Ala Asp Val Asn
        50                 55                 60

Ala Asp Asp Val Phe Gly Asp Thr Pro Leu His Leu Ala Ala Ser Leu
65                 70                 75                 80

Gly His Leu Glu Ile Val Glu Val Leu Leu Lys Tyr Gly Ala Asp Val
                85                 90                 95

Asn Ala Asp Asp Tyr Ala Gly Asn Thr Pro Leu His Leu Ala Ala Asn
                100                105                110

Thr Gly His Leu Glu Ile Val Glu Val Leu Leu Lys His Gly Ala Asp
            115                120                125

Val Asn Ala Gln Asp Lys Phe Gly Lys Thr Ala Phe Asp Ile Ser Ile
        130                135                140

Asp Asn Gly Asn Glu Asp Leu Ala Glu Ile Leu Gln Lys Leu Asn
145                150                155

<210> SEQ ID NO 48
<211> LENGTH: 159
<212> TYPE: PRT
<213> ORGANISM: Artificial Sequence
<220> FEATURE:
<223> OTHER INFORMATION: AR domain

<400> SEQUENCE: 48

Gly Ser Asp Leu Gly Lys Lys Leu Leu Glu Ala Ala Arg Ala Gly Gln
1               5                  10                 15

Asp Asp Glu Val Arg Ile Leu Met Ala Asn Gly Ala Asp Val Asn Ala
                20                 25                 30

Lys Asp Arg Phe Gly Asp Thr Pro Leu His Leu Ala Ala Asp Ile Gly
            35                 40                 45

His Leu Lys Ile Val Glu Val Leu Leu Lys His Gly Ala Asp Val Asn
        50                 55                 60

Ala Glu Asp Trp Phe Gly Asn Thr Pro Leu His Leu Ala Ala Ser Met
65                 70                 75                 80

Gly His Leu Glu Ile Val Glu Val Leu Leu Lys Tyr Gly Ala Asp Val
                85                 90                 95

Asn Ala Met Asp Asp Tyr Gly Asn Thr Pro Leu His Leu Ala Ala Asn
                100                105                110

Thr Gly His Leu Glu Ile Val Glu Val Leu Leu Lys His Gly Ala Asp
            115                120                125

Val Asn Ala Gln Asp Lys Phe Gly Lys Thr Ala Phe Asp Ile Ser Ile
        130                135                140

Asp Asn Gly Asn Glu Asp Leu Ala Glu Ile Leu Gln Lys Leu Asn
145                150                155

<210> SEQ ID NO 49
<211> LENGTH: 159
<212> TYPE: PRT
<213> ORGANISM: Artificial Sequence
<220> FEATURE:
<223> OTHER INFORMATION: AR domain

<400> SEQUENCE: 49
```

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Gln Asp Arg Trp Gly Asp Thr Pro Leu His Leu Ala Ala Ser Ala Gly
        35                  40                  45

His Leu Lys Ile Val Glu Val Leu Leu Lys Tyr Gly Ala Asp Val Asn
    50                  55                  60

Ala Asp Asp Val Phe Gly Asp Thr Pro Leu His Leu Ala Ala Ser Leu
65                  70                  75                  80

Gly His Leu Glu Ile Val Glu Val Leu Leu Lys Tyr Gly Ala Asp Val
                85                  90                  95

Asn Ala Asp Asp Tyr Ala Gly Asn Thr Pro Leu His Leu Ala Ala Asn
            100                 105                 110

Thr Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

<210> SEQ ID NO 50
<211> LENGTH: 159
<212> TYPE: PRT
<213> ORGANISM: Artificial Sequence
<220> FEATURE:
<223> OTHER INFORMATION: AR domain

<400> SEQUENCE: 50

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Arg Tyr Gly Asp Thr Pro Leu His Leu Ala Ala Asp Ile Gly
        35                  40                  45

His Leu Glu Ile Val Glu Val Leu Leu Lys Ala Gly Ala Asp Val Asn
    50                  55                  60

Ala Glu Asp Tyr Phe Gly Asn Thr Pro Leu His Leu Ala Ala Ser Tyr
65                  70                  75                  80

Gly His Leu Glu Ile Val Glu Val Leu Leu Lys Ala Gly Ala Asp Val
                85                  90                  95

Asn Ala Lys Asp Asp Tyr Gly Asn Thr Pro Leu His Leu Ala Ala Asn
            100                 105                 110

Thr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Asp Ala Gly His Glu Asp Ile Ala Glu Val Leu Gln Lys Leu Asn
145                 150                 155
```

<210> SEQ ID NO 51
<211> LENGTH: 159
<212> TYPE: PRT
<213> ORGANISM: Artificial Sequence
<220> FEATURE:
<223> OTHER INFORMATION: AR domain

<400> SEQUENCE: 51

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Arg Tyr Gly Asp Thr Pro Leu His Leu Ala Ala Asp Ile Gly
            35                  40                  45

His Leu Glu Ile Val Glu Val Leu Leu Lys Ala Gly Ala Asp Val Asn
50                  55                  60

Ala Glu Asp Tyr Phe Gly Asn Thr Pro Leu His Leu Ala Ala Ser Tyr
65                  70                  75                  80

Gly His Leu Glu Ile Val Glu Val Leu Leu Lys Ala Gly Ala Asp Val
                85                  90                  95

Asn Ala Lys Asp Asp Tyr Gly Asn Thr Pro Leu His Leu Ala Ala Asn
            100                 105                 110

Thr Gly His Leu Glu Ile Val Glu Val Leu Leu Lys Ala Gly Ala Asp
                115                 120                 125

Val Asn Ala Gln Asp Lys Ser Gly Lys Thr Pro Ala Asp Leu Ala Ala
            130                 135                 140

Asp Ala Gly His Glu Asp Ile Ala Glu Val Leu Gln Lys Leu Asn
145                 150                 155

<210> SEQ ID NO 52
<211> LENGTH: 159
<212> TYPE: PRT
<213> ORGANISM: Artificial Sequence
<220> FEATURE:
<223> OTHER INFORMATION: AR domain

<400> SEQUENCE: 52

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Arg Tyr Gly Asp Thr Pro Leu His Leu Ala Ala Asp Ala Gly
            35                  40                  45

His Leu Lys Ile Val Glu Val Leu Leu Lys Ala Gly Ala Asp Val Asn
50                  55                  60

Ala Glu Asp Tyr Phe Gly Asn Thr Pro Leu His Leu Ala Ala Ser Ala
65                  70                  75                  80

Gly His Leu Glu Ile Val Glu Val Leu Leu Lys Ala Gly Ala Asp Val
                85                  90                  95

Asn Ala Lys Asp Asp Ala Gly Asn Thr Pro Leu His Leu Ala Ala Asn
            100                 105                 110

Thr Gly His Leu Lys Ile Val Glu Val Leu Leu Lys Ala Gly Ala Asp
                115                 120                 125

Val Asn Ala Gln Asp Lys Ser Gly Lys Thr Pro Ala Asp Leu Ala Ala
            130                 135                 140

Asp Ala Gly His Glu Asp Ile Ala Glu Val Leu Gln Lys Leu Asn
145                 150                 155

<210> SEQ ID NO 53
<211> LENGTH: 159
<212> TYPE: PRT
<213> ORGANISM: Artificial Sequence
<220> FEATURE:
<223> OTHER INFORMATION: AR domain

```
<400> SEQUENCE: 53

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asn Asp Phe Leu Gly Leu Thr Pro Leu His Leu Ala Ala Ser Thr Gly
        35                  40                  45

His Leu Glu Ile Val Glu Val Leu Leu Lys Tyr Gly Ala Asp Val Asn
    50                  55                  60

Ala Ile Asp Ala Tyr Gly His Thr Pro Leu His Leu Ala Ala Asn Asn
65                  70                  75                  80

Gly His Leu Glu Ile Val Glu Val Leu Leu Lys Tyr Gly Ala Asp Val
                85                  90                  95

Asn Ala Ile Asp His Phe Gly Tyr Thr Pro Leu His Leu Ala Ala Met
            100                 105                 110

Phe Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 54
<211> LENGTH: 159
<212> TYPE: PRT
<213> ORGANISM: Artificial Sequence
<220> FEATURE:
<223> OTHER INFORMATION: AR domain

<400> SEQUENCE: 54

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asn Asp Ser Ser Gly Leu Thr Pro Leu His Leu Ala Ala Phe Tyr Gly
        35                  40                  45

His Leu Glu Ile Val Glu Val Leu Leu Lys Tyr Gly Ala Asp Val Asn
    50                  55                  60

Ala Asp Asp Asp Trp Gly His Thr Pro Leu His Leu Ala Ala His Tyr
65                  70                  75                  80

Gly His Leu Glu Ile Val Glu Val Leu Leu Lys His Gly Ala Asp Val
                85                  90                  95

Asn Ala Ile Asp Thr Arg Gly Leu Thr Pro Leu His Leu Ala Ala Ile
            100                 105                 110

Ala Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 55
<211> LENGTH: 159
<212> TYPE: PRT
<213> ORGANISM: Artificial Sequence
<220> FEATURE:
<223> OTHER INFORMATION: AR domain
```

<400> SEQUENCE: 55

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ser Asp Asp Thr Gly Leu Thr Pro Leu His Leu Ala Ala Asn Arg Gly
        35                  40                  45

His Leu Glu Ile Val Glu Val Leu Leu Lys His Gly Ala Asp Val Asn
    50                  55                  60

Ala Asn Asp Phe Ala Gly Met Thr Pro Leu His Leu Ala Ala Asn Val
65                  70                  75                  80

Gly His Leu Glu Ile Val Glu Val Leu Leu Lys Tyr Gly Ala Asp Val
                85                  90                  95

Asn Ala His Asp Asp Tyr Gly Leu Thr Pro Leu His Leu Ala Ala Asn
            100                 105                 110

Trp Arg His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Asn
145                 150                 155
```

<210> SEQ ID NO 56
<211> LENGTH: 159
<212> TYPE: PRT
<213> ORGANISM: Artificial Sequence
<220> FEATURE:
<223> OTHER INFORMATION: AR domain

<400> SEQUENCE: 56

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asn Asp Phe Leu Gly Leu Thr Pro Leu His Leu Ala Ala Ser Thr Gly
        35                  40                  45

His Leu Glu Ile Val Glu Val Leu Leu Lys Tyr Gly Ala Asp Val Asn
    50                  55                  60

Ala Ile Asp Ala Tyr Gly His Thr Pro Leu His Leu Ala Ala Asn Asn
65                  70                  75                  80

Gly His Leu Glu Ile Val Glu Val Leu Leu Lys Tyr Gly Ala Asp Val
                85                  90                  95

Asn Ala Ile Asp His Phe Gly Tyr Thr Pro Leu His Leu Ala Ala Met
            100                 105                 110

Phe Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Asn
145                 150                 155
```

<210> SEQ ID NO 57
<211> LENGTH: 159
<212> TYPE: PRT
<213> ORGANISM: Artificial Sequence
<220> FEATURE:

<223> OTHER INFORMATION: AR domain

<400> SEQUENCE: 57

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Tyr Leu Gly Leu Thr Pro Leu His Leu Ala Ala Ser Asp Gly
        35                  40                  45

His Leu Glu Ile Val Glu Val Leu Leu Lys His Gly Ala Asp Val Asn
    50                  55                  60

Ala Tyr Asp Tyr Asn Gly Leu Thr Pro Leu His Leu Ala Ala Asn Asn
65                  70                  75                  80

Gly His Leu Glu Ile Val Glu Val Leu Leu Lys Tyr Gly Ala Asp Val
                85                  90                  95

Asn Ala Phe Asp Val Ala Gly Tyr Thr Pro Leu His Leu Ala Ala Tyr
            100                 105                 110

Phe Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 58
<211> LENGTH: 159
<212> TYPE: PRT
<213> ORGANISM: Artificial Sequence
<220> FEATURE:
<223> OTHER INFORMATION: AR domain

<400> SEQUENCE: 58

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Tyr Val Gly Leu Thr Pro Leu His Leu Ala Ala Ser Ile Gly
        35                  40                  45

His Leu Glu Ile Val Glu Val Leu Leu Lys Tyr Gly Ala Asp Val Asn
    50                  55                  60

Ala Ser Asp Tyr Asn Gly Phe Thr Pro Leu Tyr Leu Ala Ala Asn Asn
65                  70                  75                  80

Gly His Leu Glu Ile Val Glu Val Leu Leu Lys Asn Gly Ala Asp Val
                85                  90                  95

Asn Ala Thr Asp Ser Phe Gly Tyr Thr Pro Leu His Leu Ala Ala His
            100                 105                 110

Tyr Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 59
<211> LENGTH: 159
<212> TYPE: PRT
<213> ORGANISM: Artificial Sequence
<220> FEATURE:
<223> OTHER INFORMATION: AR domain

<400> SEQUENCE: 59

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asp Asp Ser Leu Gly Leu Thr Pro Leu His Leu Ala Ala Ala Ser Gly
        35                  40                  45

His Leu Glu Ile Val Glu Val Leu Leu Lys Asn Gly Ala Asp Val Asn
    50                  55                  60

Ala Val Asp Gln Asn Ser Phe Thr Pro Leu Tyr Leu Ala Ala Asn Asn
65                  70                  75                  80

Gly His Leu Glu Ile Val Glu Val Leu Leu Lys Asn Gly Ala Asp Val
            85                  90                  95

Asn Ala Phe Asp Trp His Gly Thr Thr Pro Leu His Leu Ala Ala Met
            100                 105                 110

Phe Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 60
<211> LENGTH: 126
<212> TYPE: PRT
<213> ORGANISM: Artificial Sequence
<220> FEATURE:
<223> OTHER INFORMATION: AR domain

<400> SEQUENCE: 60

Gly Ser Asp Leu Gly Met Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

His Asp Thr Trp Gly Leu Thr Pro Leu His Leu Ala Ala Phe His Gly
        35                  40                  45

His Gln Glu Ile Val Glu Val Leu Leu Lys His Gly Ala Asp Val Asn
    50                  55                  60

Ala Gln Asp Phe Tyr Gly Lys Thr Pro Leu His Leu Ala Ala Leu Arg
65                  70                  75                  80

Gly His Leu Glu Ile Val Glu Val Leu Leu Lys Tyr Gly Ala Asp Val
            85                  90                  95

Asn Ala Gln Asp Gln Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 61
<211> LENGTH: 159
<212> TYPE: PRT
<213> ORGANISM: Artificial Sequence
<220> FEATURE:
<223> OTHER INFORMATION: AR domain

<400> SEQUENCE: 61

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Glu Asp Tyr Leu Gly His Thr Pro Leu His Leu Ala Ala Ser Thr Gly
            35                  40                  45

His Leu Glu Ile Val Glu Val Leu Leu Lys Tyr Gly Ala Asp Val Asn
        50                  55                  60

Ala Lys Asp Arg Asn Gly Leu Thr Pro Leu Tyr Leu Ala Ala Asn Asn
65                  70                  75                  80

Gly His Leu Glu Ile Val Glu Asp Leu Leu Lys Tyr Gly Ala Asp Val
                85                  90                  95

Asn Ala Asp Asp Asp Asn Gly Thr Thr Pro Leu His Leu Ala Ala Ile
            100                 105                 110

Phe Gly His Leu Glu Ile Val Glu Val Leu Leu Lys Tyr Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155
```

<210> SEQ ID NO 62
<211> LENGTH: 167
<212> TYPE: PRT
<213> ORGANISM: Artificial Sequence
<220> FEATURE:
<223> OTHER INFORMATION: AR domain

<400> SEQUENCE: 62

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Arg Phe Gly Asp Thr Pro Leu His Leu Ala Ala Asp Ile Gly
            35                  40                  45

His Leu Lys Ile Val Glu Val Leu Leu Lys His Gly Ala Asp Val Asn
        50                  55                  60

Ala Glu Asp Trp Phe Gly Asn Thr Pro Leu His Leu Ala Ala Ser Met
65                  70                  75                  80

Gly His Leu Glu Ile Val Glu Val Leu Leu Lys Tyr Gly Ala Asp Val
                85                  90                  95

Asn Ala Met Asp Asp Tyr Gly Asn Thr Pro Leu His Leu Ala Ala Asn
            100                 105                 110

Thr Gly His Leu Glu Ile Val Glu Val Leu Leu Lys His Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Gly Gly
145                 150                 155                 160

Gly Ser Gly Gly Gly Ser Cys
                165
```

<210> SEQ ID NO 63
<211> LENGTH: 6
<212> TYPE: PRT
<213> ORGANISM: Artificial Sequence
<220> FEATURE:

```
<223> OTHER INFORMATION: peptide motif of capping module

<400> SEQUENCE: 63

Arg Glu Leu Leu Lys Ala
1               5

<210> SEQ ID NO 64
<211> LENGTH: 6
<212> TYPE: PRT
<213> ORGANISM: Artificial Sequence
<220> FEATURE:
<223> OTHER INFORMATION: peptide motif of capping module

<400> SEQUENCE: 64

Arg Ile Leu Lys Ala Ala
1               5

<210> SEQ ID NO 65
<211> LENGTH: 6
<212> TYPE: PRT
<213> ORGANISM: Artificial Sequence
<220> FEATURE:
<223> OTHER INFORMATION: peptide motif of capping module

<400> SEQUENCE: 65

Arg Ile Leu Leu Ala Ala
1               5
```